United States Patent
Tsuchino et al.

(10) Patent No.: US 7,365,337 B2
(45) Date of Patent: Apr. 29, 2008

(54) RADIOGRAPHIC IMAGE DETECTION DEVICE AND RADIOGRAPHIC IMAGING SYSTEM

(75) Inventors: Hisanori Tsuchino, Hachioji (JP); Yasuaki Tamakoshi, Hino (JP); Hiromu Ohara, Hachioji (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 225 days.

(21) Appl. No.: 11/225,803

(22) Filed: Sep. 13, 2005

(65) Prior Publication Data

US 2006/0054829 A1 Mar. 16, 2006

(30) Foreign Application Priority Data

Sep. 16, 2004 (JP) ............................. 2004-269974
Jan. 31, 2005 (JP) ............................. 2005-023643
Jan. 31, 2005 (JP) ............................. 2005-023659

(51) Int. Cl.
*G01T 1/24* (2006.01)
(52) U.S. Cl. ................................ 250/370.09
(58) Field of Classification Search ............ 250/370.09
See application file for complete search history.

(56) References Cited

U.S. PATENT DOCUMENTS

| | | | | |
|---|---|---|---|---|
| 5,227,927 A * | 7/1993 | Fukushima et al. | ............ | 360/69 |
| 5,375,246 A * | 12/1994 | Kimura et al. | ............... | 365/229 |
| 5,877,501 A * | 3/1999 | Ivan et al. | ............... | 250/370.09 |
| 6,344,652 B1 * | 2/2002 | Shoji | ...................... | 250/370.09 |
| 7,072,443 B2 * | 7/2006 | Schick et al. | ............... | 378/98.8 |
| 7,109,491 B2 * | 9/2006 | Shinden | ................. | 250/370.09 |
| 7,162,067 B2 * | 1/2007 | Motoki | ....................... | 382/132 |
| 7,193,219 B2 * | 3/2007 | Schick et al. | ............ | 250/370.11 |
| 7,239,685 B2 * | 7/2007 | Petrick et al. | ............... | 378/116 |
| 7,289,602 B1 * | 10/2007 | Polichar et al. | ............ | 378/98.8 |
| 2002/0044211 A1 | 4/2002 | Tujii et al. | | |
| 2004/0065837 A1 * | 4/2004 | Schick et al. | ............ | 250/370.08 |
| 2004/0066898 A1 * | 4/2004 | Schick et al. | ............... | 378/98.9 |
| 2005/0207534 A1 * | 9/2005 | Petrick et al. | ............... | 378/114 |
| 2006/0017028 A1 * | 1/2006 | Ohara et al. | ................. | 250/580 |
| 2006/0054822 A1 * | 3/2006 | Tsuchino | ................. | 250/336.1 |
| 2006/0193436 A1 * | 8/2006 | Schick et al. | ............... | 378/98.8 |
| 2007/0153980 A1 * | 7/2007 | Butzine et al. | ............. | 378/198 |

FOREIGN PATENT DOCUMENTS

| | | |
|---|---|---|
| JP | 2002-165142 A | 6/2002 |
| JP | 2002-200064 A | 7/2002 |
| JP | 2003-18033 A | 1/2003 |
| JP | 2003-42976 A | 2/2003 |

\* cited by examiner

*Primary Examiner*—David Porta
*Assistant Examiner*—David S Baker
(74) *Attorney, Agent, or Firm*—Frishauf, Holtz, Goodman & Chick, P.C.

(57) ABSTRACT

A radiographic imaging system includes: a plurality of states of operation, a radiographic image detection device that detects irradiated radiation to obtain radiographic image information, a console capable of communicating with the radiographic image detection device, a status memory which stores the information of operation concerning the state of operation after end of charging or replacing the battery; and the radiographic image detection device includes: power supply source having a rechargeable or replaceable battery to supply power to a plurality of units driven by the power, a control unit that stores in the status memory the information of operation, before the end of charging or replacing the battery, and then after the end of charging or replacing of the battery, controls the state of operation of the units driven by the power in response to the information of operation stored in the status memory.

16 Claims, 13 Drawing Sheets

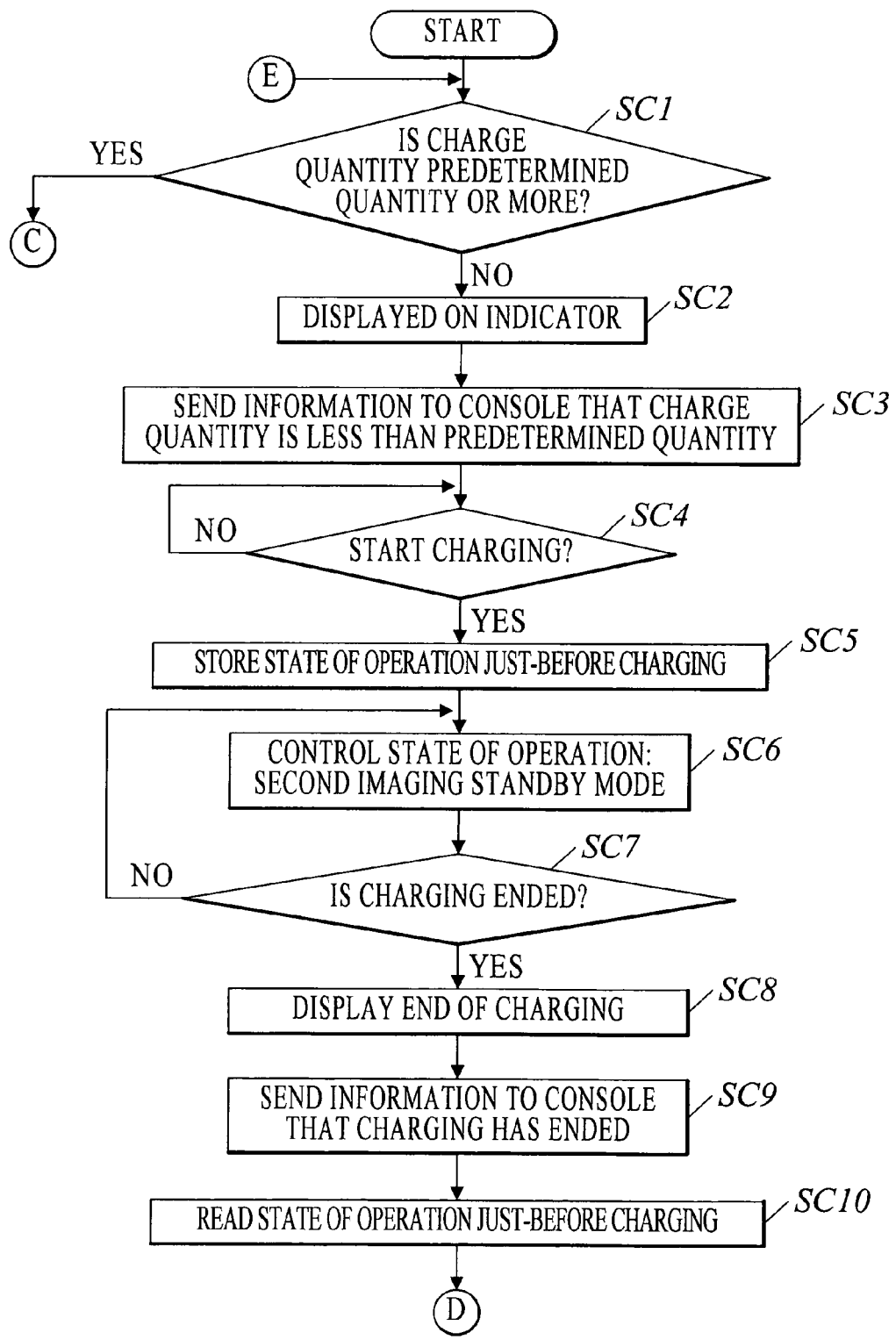

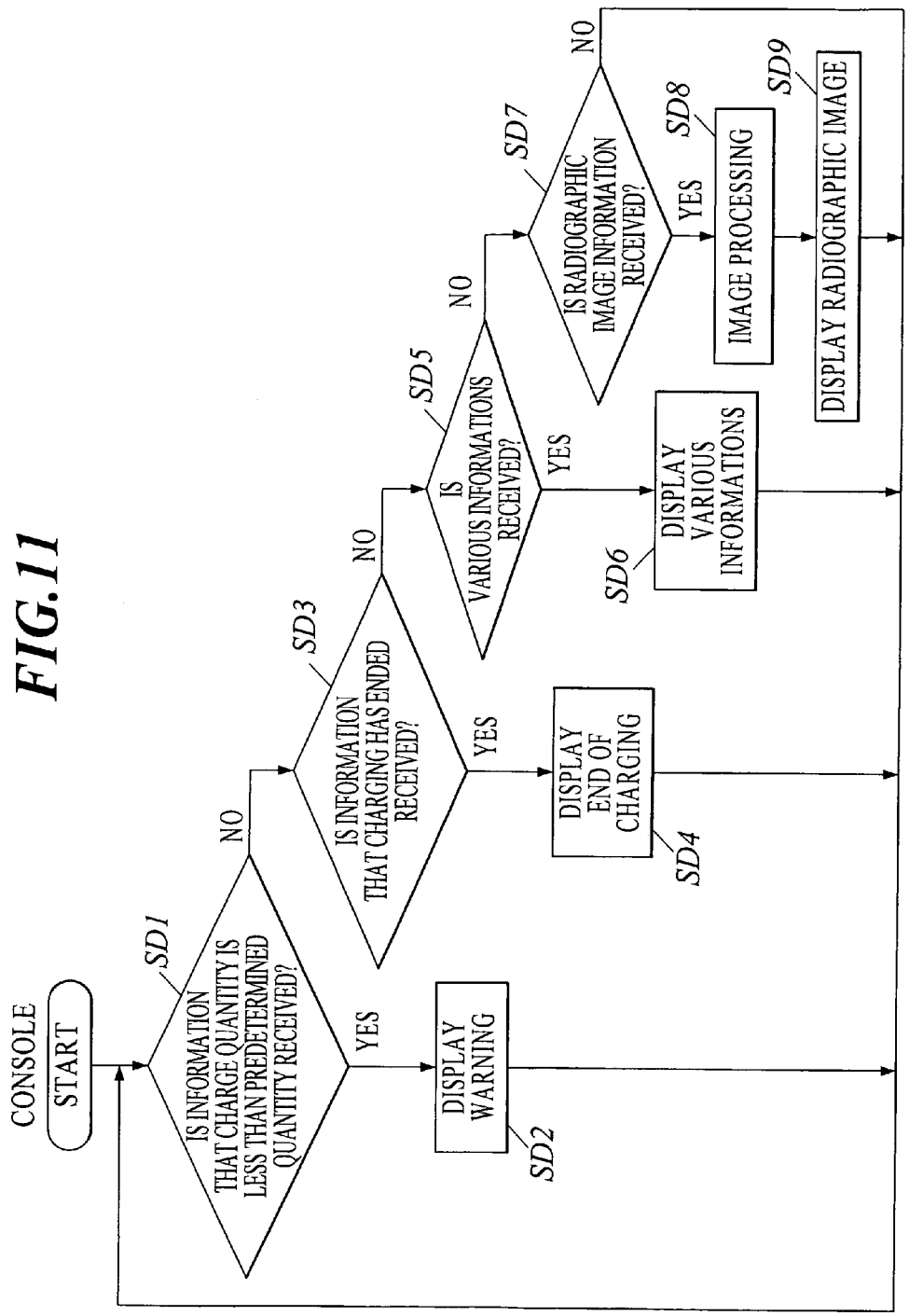

RADIOGRAPHIC IMAGE DETECTION DEVICE AND RADIOGRAPHIC IMAGING SYSTEM

BACKGROUND OF THE INVENTION

1. Field of the Invention

The present invention relates to a radiographic image detection device and a radiographic imaging system

2. Description of the Related Art

In the field of radiographic imaging for medical diagnosis, there has been widely known a radiographic imaging system in which a subject is irradiated with radiation and an intensity distribution of the radiation transmitted through the subject is detected to obtain a radiographic image of the subject. In a recent radiographic imaging system, there has been developed and used a radiographic image detection device called a "flat panel detector" (hereinafter,.referred to as "FPD"), which is formed as a thin flat plate having a large number of photoelectric conversion elements arranged thereon in a matrix. The FPD detects the radiation transmitted through the subject, photoelectricaly converts the detected radiation into electric signals, and performs image processing on the converted electric signals, thereby obtaining easily and rapidly the radiographic image of the subject.

The radiographic image detection device is broadly classified into a stationary detection device installed as a part of the system at a predetermined position and a portable (cassette type) detection device to be freely carried. From a viewpoint of easiness in carrying and handling, utilization of the cassette type radiographic image detection device has been widely studied recently.

Such a cassette type radiographic image detection device needs to have a power supply installed therein for driving the image detection device, and a built-in battery or a replaceable battery is plausible. There has been actually known such radiographic image detection device that has a replaceable battery therein as a power supply and can be repeatedly used with appropriate replacement of the battery with a new one (for example, refer to JP 2002-181942A).

However, in case that the battery needs to be charged or replaced in the middle of continuous imaging operation, it is preferable from a viewpoint of efficient imaging operation to go to the next imaging operation upon end of charging or replacing the battery. However, concerning photodiodes or thin film transistors (hereinafter referred to as 'TFT") comprising the radiographic image detection device, it became obvious that efficiency of the entire radiographing workflow is influenced by these units, since its function and operation do not stabilize immediately after supplying power if the power supply is once stopped.

On the other hand, if power is always supplied to all units of the radiographic image detection device, power consumption increases. This leads to a problem of reduction in operation efficiency due to shorter time of operation, particularly in a radiographic image detection device that is operated by an internal battery without supplying power from an external power source. Consequently, it became obvious that efficiency of the entire radiographing workflow is influenced.

Further, some components included in the radiographic image detection device, such as photodiodes or TFTs, deteriorate within time elapse during power supply. For this reason, if power is kept supplied to these components that deteriorate within time, even while imaging operation is not operated for a long period of time, a problem also arises in that deterioration of these components causes the lifetime of the radiographic image detection device to be shortened.

SUMMARY OF THE INVENTION

The present invention is:
a radiographic imaging system comprising:
a radiographic image detection device which has a plurality of states of operation and detects irradiated radiation to obtain radiographic image information; and
a console capable of communicating with the radiographic image detection device,
a status memory to store information of operation associated with a state of operation after end of charging or replacing the battery,
wherein the information of operation is stored in the status memory before the end of charging or replacing the battery, and
the radiographic image detection device comprises:
a power supply source having a rechargeable or replaceable battery to supply power to a plurality of units driven by the power; and
a control unit which controls power supply from the power supply source to the units driven by the power in response to the information of operation stored in the status memory after the end of charging or replacing the battery.

In the present invention, advantageous is achieved by enhancing the efficiency of the entire radiographing workflow as well as the lifetime of components of the radiographic image detection device.

Here in the present invention, "A comprising B and C" means "(A comprising B) and (A comprising C)". That is, B and C are not limited to conditions wherein component composing B and component composing C do not overlap. For example, part of component composing B may be also part of component composing C, entire component composing B may be part of component composing C, part of component composing B may be entire component composing C, and entire component composing B may be entire component composing C.

BRIEF DESCRIPTION OF THE DRAWINGS

The present invention will become more fully understood from the detailed description given hereinafter and the accompanying drawings which are given by way of illustration only, and thus are not intended as a definition of the limits of the scope of the invention, and wherein:

FIGS. 10a and 10b are flow charts showing operations in time sequence executed in the radiographic image detection device when a radiographic imaging system according to a second embodiment runs;

FIG. 11 is a flow chart showing operations in time sequence executed in the console when a radiographic imaging system according to a second embodiment.

DETAILED DESCRIPTION OF THE PREFERRED EMBODIMENTS

Figure 1:
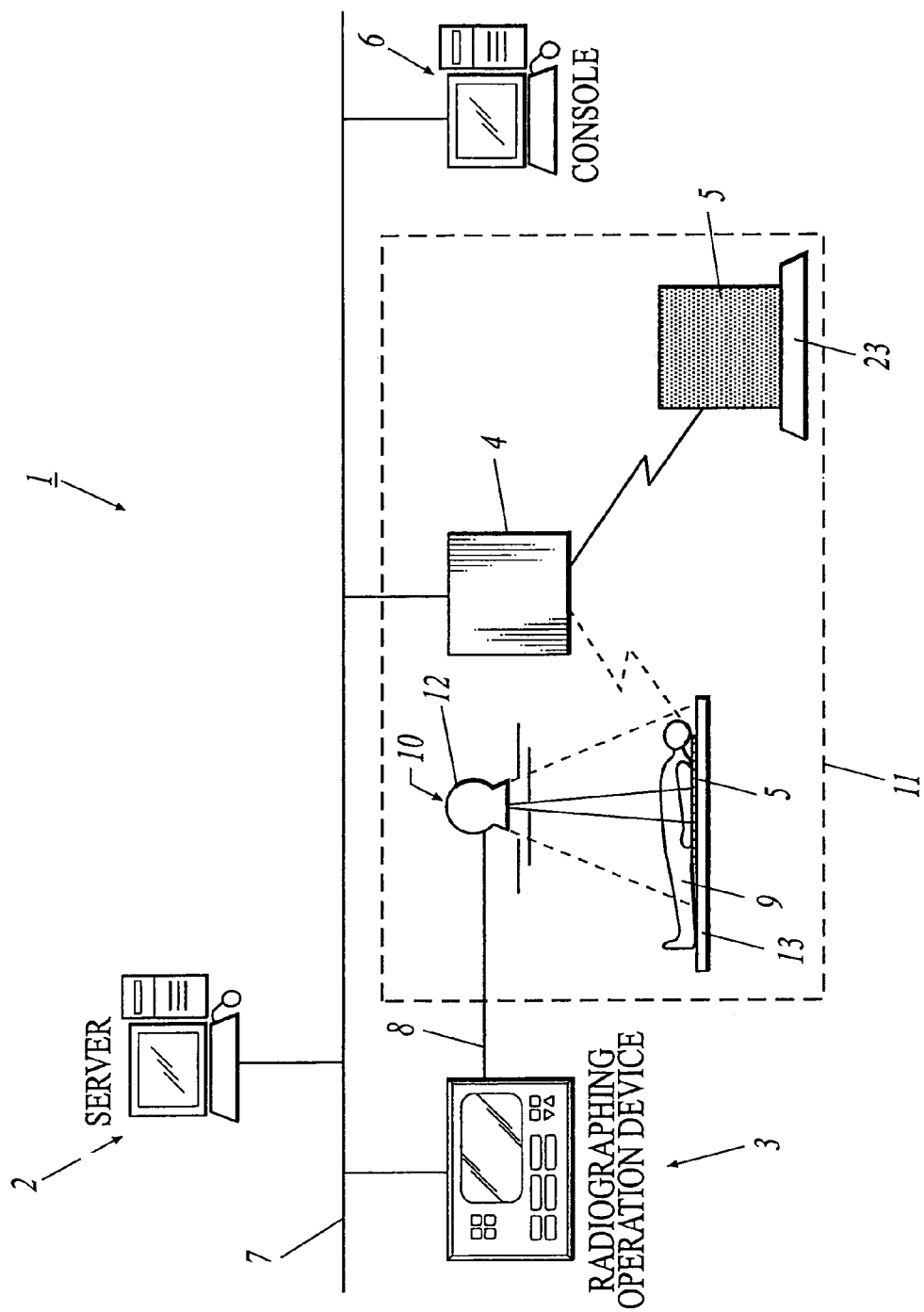
FIG. 1 is a view showing a schematic configuration illustrating one embodiment of a radiographic imaging system.

An object of the embodiment is to provide a radiographic image detection device and a radiographic imaging system, which can enhance the efficiency of the entire radiographing workflow as well as the lifetime of components of the radiographic image detection device.

In accordance with a first aspect of the-embodiment, a radiographic image detection device which has a plurality of states of operation and detects irradiated radiation to obtain radiographic image information, comprises;

a power supply source having a rechargeable or replaceable battery to supply power to a plurality of units driven by the power; and a status memory unit which stores information of operation, concerning the state of operation after end of charging or replacement of the battery, and a control unit which controls power supply from the power supply source to the units driven by the power in response to the information of operation stored in the status memory after the end of charging or replacing the battery.

In accordance with a second aspect of the embodiment, a radiographic image detection system comprises;

a radiographic image detection device which has a plurality of states of operation and detects irradiated radiation to obtain radiographic image information;

a console capable of communicating with the radiographic image detection device;

a status memory unit which stores the information of operation concerning the state of operation after the end of charging or replacing the battery, whereas the information of operation is stored in the status memory before the end of charging or replacing the battery, and the radiographic image detection device comprises;

a power supply source having a rechargeable or replaceable battery to supply power to a plurality of units driven by the power; and a control unit which controls power supply from the power supply source to the units driven by the power in response to the information of operation stored in the status memory after the end of charging or replacing the battery.

In the embodiment according to the first and second aspect of the invention, advantageous is achieved by enhancing the efficiency of the entire radiographing workflow as well as the lifetime of components of the radiographic image detection device.

Preferably in accordance with the first and second aspect of the embodiment, the control unit stores the information of operation in the status memory according to the state of operation just before charging or replacing the battery.

In this case, after end of charging or replacing the battery, the state of operation of the detection device is brought into a state of operation based on the state of operation just before the charging or replacement of the battery. For example, when the battery is charged or replaced in the imaging ready state, the detection device, after end, is controlled to be in the imaging ready state or the imaging standby state, and when the battery is charged or replaced in the imaging standby state, the detection device, after end, is controlled to be in the imaging standby state. Accordingly, at the time of end of charging or replacing the battery, a proper state of operation is resumed, even if the operator does not set the state of operation of the detection device within grasping the state of operation, so that an effective imaging operation can be achieved by preventing deterioration of components and increase in power consumption.

Preferably in the embodiment according to the first and second aspect of the invention, the state of operation after end can be selectively set, and the control unit stores the information of operation in the status memory according to the selectively set state of operation after end of charging or replacing the battery.

In this case, by selectively setting a state of operation after end of charging or replacing the battery before end of charging or replacing the battery, a state of operation after end of charging or replacing the battery can be attained as desired. As a result, an effective imaging operation can be achieved by preventing deterioration of components and increase in power consumption.

In this case, more preferably, it is selectable whether the state of operation after end of charging or replacing the battery is previously set or arbitrarily set, and the information of operation is stored in the status memory based on the state of operation being selected and set.

At this time, it is selectable whether the state of operation after end of charging or replacing the battery is previously set, or arbitrarily set. Therefore, when the charging or replacement of the battery is completed, for example, the state of operation can be set to a previously set one, or be arbitrarily set depending on conditions, such as whether the time after end of charging or replacing the battery falls within consultation hours or not, or to the number of remaining imaging orders, or the like. As a result, a proper state of operation can be resumed depending on the condition of the radiographic image detection device, so that an effective imaging operation can be achieved by preventing deterioration of components and increase in power consumption.

In this case, more preferably, as an arbitrarily set state of operation, an imaging ready state capable of detecting the radiation;

an imaging standby state that requires less power consumption than the imaging ready state with power supplied to at least one unit of the units driven by the power; and an imaging stop state in which power supply is stopped for all the units driven by the power;

can be set.

At this time, there may be set the imaging ready state, the imaging standby state or the imaging stop state as a state of operation of the detection device after end of charging or replacing the battery, so that a state of operation after end of charging or replacing the battery can be set to a proper state of operation depending on the condition. As a result, an effective imaging operation can be achieved by preventing deterioration of components and increase in power consumption.

Preferably in accordance with the first and second aspect of the embodiment, a plurality of states of operation include:
an imaging ready state capable of detecting the radiation;
an imaging standby state that requires less power consumption than the imaging ready state with power supplied to at least one unit of the units driven by the power; and
an imaging stop state in which power supply is stopped for all the units driven by the power.

In this case, since there is the imaging ready state, the imaging standby state or the imaging stop state as a state of operation of the radiographic image detection device, deterioration of components and increase in power consumption can be prevented.

In this case, more preferably,
imaging standby state has a plurality of imaging standby modes having different power consumption.

At this time, since the imaging standby state has a plurality of modes, more appropriate state of operation can be selected as a state of operation, so that deterioration of components and increase in power consumption can be prevented. Particularly, photodiodes, TFTs and the like need a long time to resume a stable state suitable for imaging if power supply is once stopped. To the contrary, these elements have characteristics of deterioration within time elapse during power supply. For these reasons, power supply to the photodiodes and TFTs is preferably not stopped in such imaging environment that continuous imaging is performed with interruption of short-time rest, and the power supply to these components is preferably stopped in such imaging environment that imaging is not performed for a long period of time. For a part such as a signal reading circuit that particularly has large power consumption, it is preferable to hold down power consumption by stopping power supply as far as possible. Therefore, by switching power supply depending on the characteristic of each component, more efficient imaging operations can be achieved.

In this case, more preferably,
control unit controls the state of operation of the units driven by the power so that the detection device, while charging or replacing the battery, is in the imaging standby mode that requires the minimum power consumption among the plurality of imaging standby modes.

At this time, since imaging is not allowed while charging or replacing the battery, power consumption in this term can be reduced, however, not all the units driven by the power is not supplied with power. Accordingly, start-up time after end of charging or replacing the battery can be shortened, as well as deterioration of components and increase in power consumption can be prevented. Moreover, in case that the communication unit is powered in the mode in which power consumption is regulated to a minimum, it is allowed to receive signals from external device even while charging or replacing the battery, and start controlling for the next imaging operation immediately, thereby preventing reduction in operation efficiency.

Preferably in accordance with the first and second aspect of the embodiment,
the battery is replaceable, and the detection device is brought into a turned-off state while the battery is being detached or attached.

In this case, since the detection device is in a turned-off state while replacing the battery, the operator can be prevented from being exposed to danger of getting an electric shock while the operator replaces the battery.

Preferably in accordance with the first and second aspect of the embodiment,
radiographic image detection device is a cassette type flat panel detection device that detects the irradiated radiation, converts the radiation into electric signals to be stored, reads the stored electric signals and obtains radiographic image information.

In this case, since the radiographic image detection device is a cassette type FPD, the detection device can be easily carried without restriction of imaging place, so the flexibility of imaging can be improved and a proper state of operation can be selected after end of charging or replacing the battery. As a result, deterioration of components and increase in power consumption can be prevented.

The following description only represents the most plausible form the inventor recognizes. Therefore, though there may be expressions that may be taken as a definition of the present invention and claims, these expressions are used only for defining the most plausible form which the inventor recognizes, and thus are not intended as a definition of the present invention and claims.

First Embodiment

An embodiment of the present invention will be described below with reference to FIGS. 1 to 9.

FIG. 1 is a view showing a schematic configuration of one embodiment of a radiographic imaging system employing a radiographic image detection device according to the invention.

The radiographic imaging system 1 concerning the embodiment is, for example, a system applied to radiographic imaging performed in a hospital. As shown in FIG. 1, server 2 for managing various kinds of information concerning imaging and patient, imaging operation device 3 for performing operations relating to the radiographic imaging, base station 4 for performing communication via wireless communication system such as a wireless LAN (Local Area Network), and console 6, operating radiographic image detector 5 and executing image processing on a radiographic image detected by the radiographic image detection device 5 are connected through network server 7.

The imaging operation device 3 is connected by cable 8 to radiographic imaging device 10, irradiating the patient as subject 9 with radiation to capture a radiographic image. The radiographic imaging device 10 and the radiographic image detection device 5 are, for example, each installed in one imaging room 11, and radiographic image information can be obtained by operating the radiographic imaging device 10 with the imaging operation device 3 and detecting the radiographic image with the radiographic image detection device or 5. Alternatively, one imaging room 11 may be provided with a plurality of radiographic image detection devices 5.

The network 7 can be a communication line dedicated to the system. However, the network 7 is preferably an existing line such as Ethernet (registered trademark), since flexibility of system configuration would otherwise be decreased, or for other reasons. In addition to the above exemplified devices, the network 7 may be connected thereto a plurality of imaging operation devices 3 to operate radiographic imaging devices 10 installed in other imaging rooms 11, radiographic image detection devices 5, and consoles 6.

The imaging operation device 3 comprises an operation panel and the like to operate the radiographic imaging device 10, for example, input operation unit to input signals for imaging conditions or the like; a display unit for displaying information on the imaging conditions, various instructions, and the like; and a power supply unit to supply power to the radiographic imaging device 10 (none of them are shown).

The radiographic imaging device 10 is disposed inside the imaging room 11, having a radiation source 12 that generates radiation by the tube voltage applied thereto. As the radiation source 12, for example, a radiation tube is used. The radiation tube generates the radiation by accelerating electrons generated by thermal excitation under a high voltage to have the electrons collide with a cathode.

The radiographic image detection device 5 detects radiation, which is radiated from the radiation source 12 of the radiographic imaging device 10 and transmitted through subject 9, to capture a radiographic image. At the time of imaging, the detector 5 is disposed within an area irradiated by the radiation emitted from the radiation source 12. The radiographic image detector 5 is exposed, for example, as shown in FIG. 1, between subject 9 and bed 13 on which subject 9 is laid. However, the position thereof is not limited thereto. For example, there may be provided below the bed a detection device mounting opening (not shown), through which the radiographic image detection device 5 is mounted, and the detection device 5 may be inserted into the detection device mounting opening.

The radiographic image detection device 5 is a flat-panel type. A structure of the radiographic image detection device 5 will be described below with reference to FIGS. 2 and 3.

Figure 2:
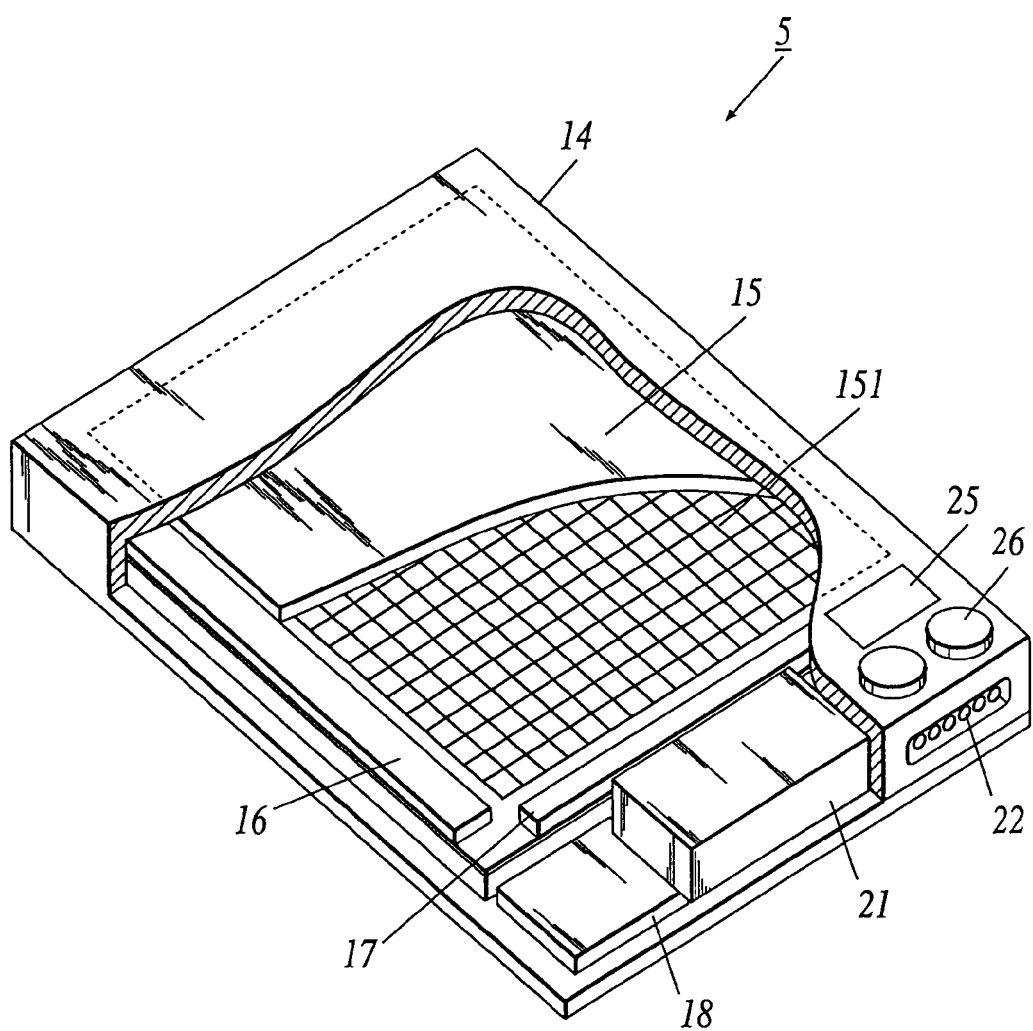
FIG. 2 is a perspective view showing a structure of main parts of a radiographic image detection device.

As shown in FIG. 2, the radiographic image detection device 5 includes a housing 14 to protect the inside of the detection device, and is configured to be portable as a cassette.

Inside the housing 14, there is formed a layered imaging panel 15 to convert irradiated radiation into electric signals. At the surface of irradiated side of the imaging panel 15, there is provided a light-emitting layer (not shown) to emit light according to intensity of the radiation incident thereto.

The light-emitting layer is one generally called a scintillator layer, and, for example, contains phosphor as a main component and outputs an electromagnetic wave having a wavelength from 300 to 800 nm, that is, an electromagnetic wave (light) ranging from ultraviolet light to infrared light with visible light in the middle.

As the phosphor to be used in the light-emitting layer, for example, phosphor containing $CaWO_4$ or the like as a basic substance, and phosphor consisting of activator and basic substance such as CsI: Tl, $Gd_2O_2S$: Tb, and ZnS: Ag, may be used. Further, phosphor represented by a general formula (Gd, M, Eu)$_2O_3$, where M is a rare-earth element, can be used. Particularly, CsI:Tl and $Gd_2O_2S$:Tb are preferable because of high radiation absorption and light-emitting efficiencies thereof. By using these substances, a low-noise and high-quality image can be obtained.

On the surface, which is opposite to the surface to be irradiated by the radiation of the light-emitting layer, there is formed a signal detection unit 151 which converts the electromagnetic wave (light) output from the light-emitting layer into electric energy and stores the energy. The detection unit 151 then outputs an image signal based on the stored electric energy.

Figure 3:
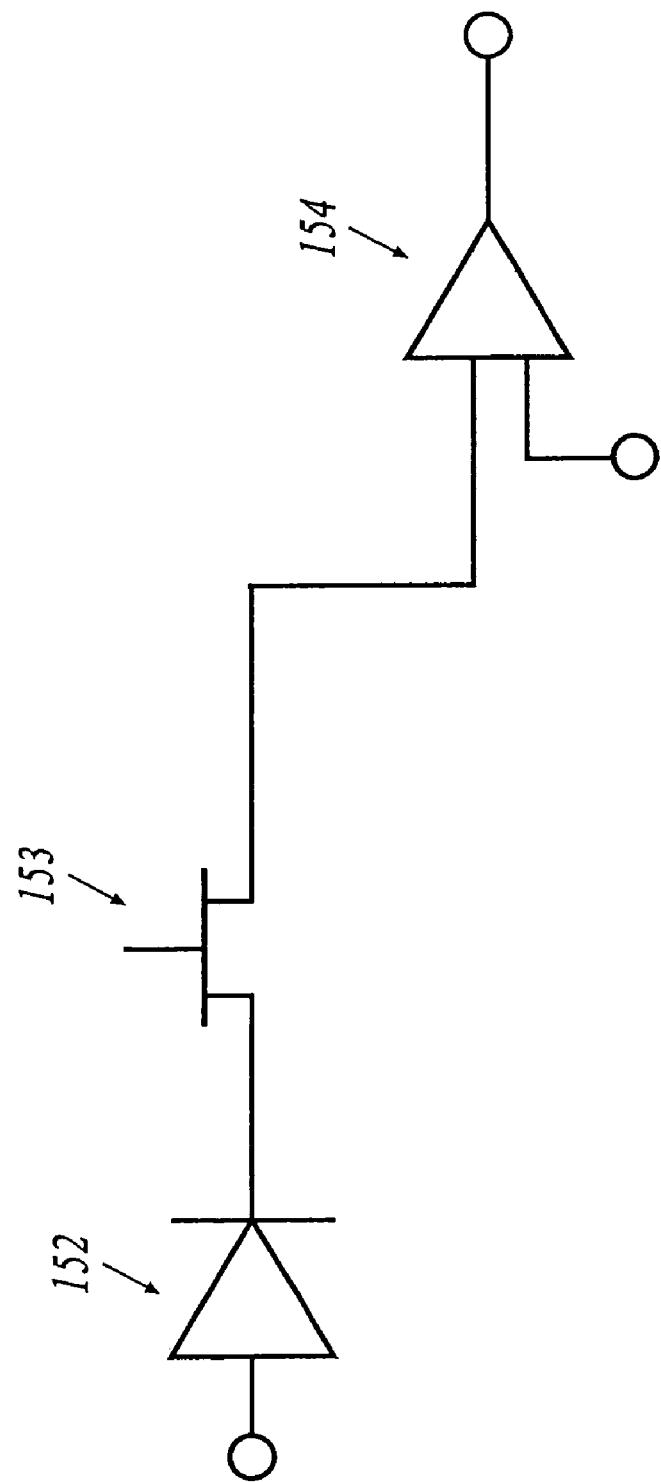
FIG. 3 is a configuration view of an equivalent circuit for one pixel in a photoelectric conversion unit constituting a photoelectric conversion layer.

A circuit configuration of the imaging panel 15 will now be described. FIG. 3 is an equivalent circuit diagram of a photoelectric conversion unit for one pixel constituting the signal detection unit 151.

As shown in FIG. 3, the photoelectric conversion unit for one pixel includes a photodiode 152, and a thin film transistor (hereinafter referred to as "TFT") 153 extracting the electric energy stored in the photodiode 152 as an electric signal by switching. The extracted electric signal is amplified by an amplifier 154 to such level that a signal reading circuit 17 can detect the amplified electric signal.

Figure 4:
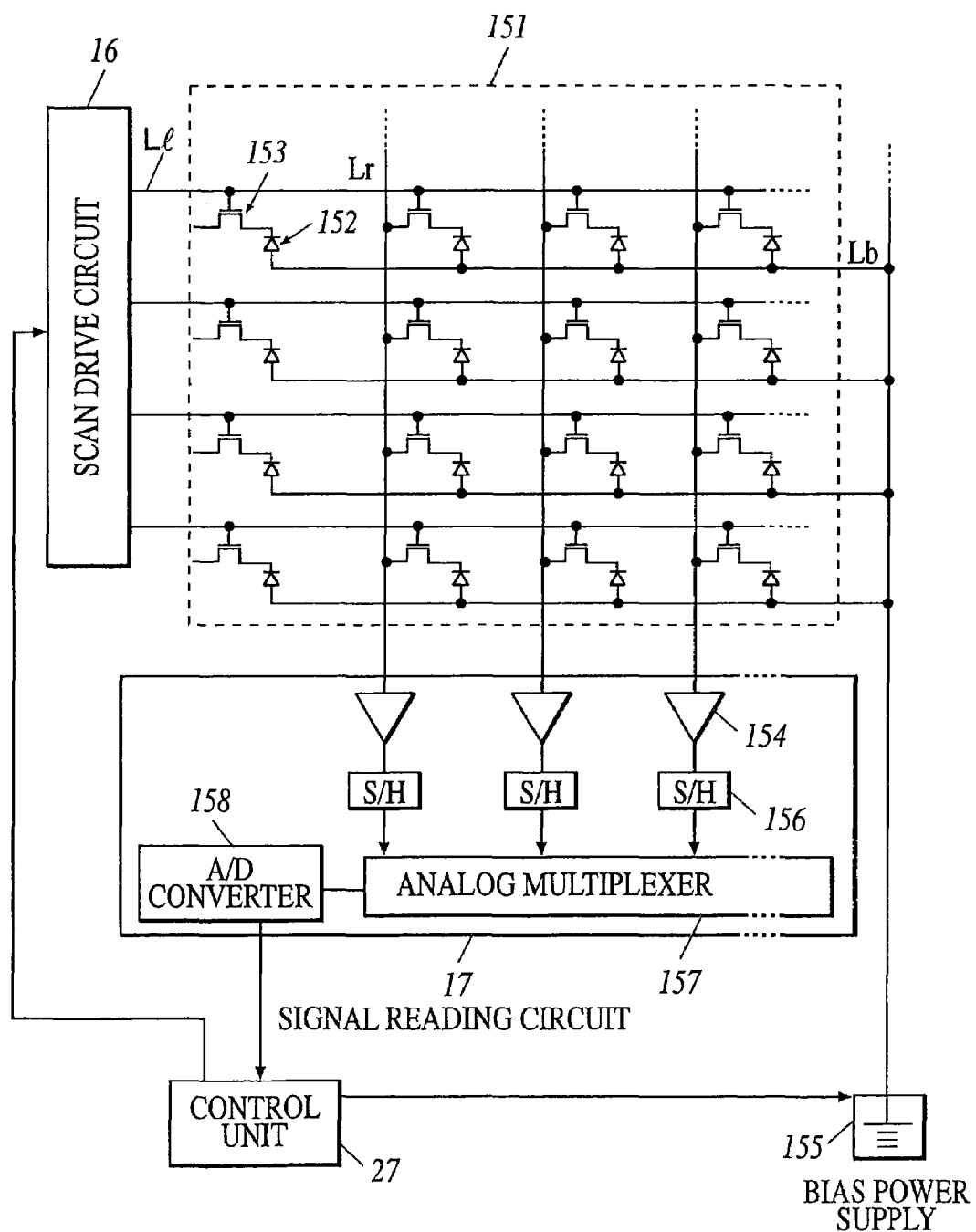
FIG. 4 is a configuration view of an equivalent circuit in which the photoelectric conversion units shown in FIG. 3 are arranged two-dimensionally.

To the amplifier 154, a reset circuit (not shown) including the TFT 153 and a capacitor is connected. The reset circuit performs a reset operation, which is resetting the stored electric signal, by switching on the TFT 153. The photodiode 152 may be a photodiode simply having a parasitic capacitance, or may include additional capacitors in parallel so as to improve dynamic ranges of the photodiode 152 and the photoelectric conversion unit. FIG. 4 is an equivalent circuit diagram in which the above-described photoelectric conversion units are arranged two-dimensionally. Between the pixels, scan lines Ll and signal lines Lr are arranged orthogonally. TFT 153 is connected to each photodiode 152, and one end of the photodiode 152, which the TFT 153 is connected, is connected to the signal line Lr. The other end of the photodiode 152 is connected to the other end of the adjacent photodiode 152 arranged on each row, and connected to a bias power supply 155 through a common bias line Lb. One end of the bias power supply 155 is connected to a control unit 27, and thus a voltage is applied to the photodiodes 152 through the bias line Lb depending on an instruction from the control unit 27. The TFTs 153 arranged on each row are connected to their common scan line Ll, and each scan line Ll is connected to the control unit 27 through a scan drive circuit 16. Similarly, the photodiodes 152 arranged on each column are connected to their common signal line Lr, and connected to the signal reading circuit 17 controlled by the control unit 27.

In the signal reading circuit 17, an amplifier 154, a sample-hold circuit 156, an analog multiplexer 157, and an A/D converter 158 are arranged on the common signal line Lr.

The TFT 153 may be an inorganic semiconductor series or one using an organic semiconductor, which is used in a liquid crystal display and the like.

Moreover, although the photodiodes 152 are used as the photoelectric conversion elements in this embodiment, solid-state imaging elements other than the photodiodes may be used as the photoelectric conversion elements.

As shown in FIG. 2, at the side of the signal detection unit 151, are disposed the scan drive circuit 16 to scan and drive the respective photoelectric conversion elements by sending pulses to the photoelectric conversion elements, and the signal reading circuit 17 to read the electric energy stored in the respective photoelectric conversion elements.

The radiographic image detection device 5 includes an image memory 18 which is, for example, a rewritable read only memory such as a RAM (Random Access Memory) or a flash memory. The image memory 18 stores an image signal output from the imaging panel 15. The image memory 18 may be a built-in memory or a removable memory such as a memory card.

Further, the radiographic image detection device 5 is provided with a rechargeable battery 21 as a power supply source to supply power to a plurality of units driven by the power (for example, the scan drive circuit 16, the signal reading circuit 17, a communication unit (described later), the image memory 18, a charge quantity detector (not shown), an indicator 25 (described later), an input operation unit 26 (described later), the imaging panel 15, and the like) constituting the radiographic image detection device 5.

As the rechargeable battery 21, a rechargeable battery, such as a nickel-cadmium battery, a nickel-metal hydride battery, a lithium-ion battery, a small-sized sealed lead-acid battery, a lead-acid battery, or the like may be used. Additionally, a fuel cell may be used in place of rechargeable battery 21.

At one end of the housing 14 charging terminals 22 are provided. As shown in FIG. 1, for example, by placing the radiographic image detection device 5 on a charging device 23, such as a cradle, which is connected to an external power supply, the housing-side terminals 22 are coupled to terminals (not shown) on the charging device 23 to charge the rechargeable battery 21. Here, the shape of the rechargeable battery 21 as a power supply source is not limited to what is illustrated in FIG. 2. For example, a plate shaped battery may be provided in parallel with the imaging panel 15. By forming the battery into such a shape, the area of the imaging panel 15 can be increased, and the imaging-enabled area can be expanded.

Further, the radiographic image detection device 5 is provided with a communication unit 24 (refer to FIG. 5) for sending and receiving various signals to and from an external device such as the console 6. The communication unit 24, for example, transmits an image signal output from the imaging panel 15 to the console 6, and receives imaging start signal or the like sent from the console 6 or the like.

Moreover, at one end of the surface of the housing 14, the indicator 25 is provided for displaying a charging state of the rechargeable battery 21, various operation statuses and the like. An operator can visually confirm the charging states of the battery 21 and the like of the radiographic image detection device 5 through the indicator 25.

On the outer side of the housing 14, is provided the input operation unit 26, through which the operator such as a radiologist inputs and sets the imaging condition, identification information of the patient, various instructions, and the like. Note that contents that can be input from the input operation unit 26 are not limited to those illustrated here. The input operation unit 26 also functions as a selective means when previously setting a state of operation of the radiographic image detection device 5. The state of operation of the radiographic image detection device 5 in the embodiment has an "imaging ready state", an "imaging standby state" and an "imaging stop state". In this embodiment, from the input operation unit 26, state of operation after end of charging can be selectively set among "imaging ready state", "imaging standby state", or "imaging stop state", or set a state of operation that corresponds to the state of operation just before charging.

The imaging ready state is a state in which every driving unit used in a series of imaging operations out of components included in the radiographic image detection device 5 is working, that is, power is supplied to all units driven by the power. As for the units driven by the power used in the series of imaging operations are scan drive circuit 16, signal reading circuit 17, photodiodes 152, TFTs 153, image memory 18, and communication unit 24. In addition, as the series of imaging operations, initializing image information in image memory 18, storing electric energy generated depending on the irradiated radiation at photodiode 152, reading electric signals by scan drive unit 16 and signal reading circuit 17, and transmitting image signals by communication unit 24 can be mentioned. In the imaging ready state, it is possible to perform the series of imaging operations. At initialization, there is performed the reset operation and a dark-image reading operation in the imaging panel 15.

The imaging standby state is a state comprising "first imaging standby mode" in which power consumption is less than that of the imaging ready state, and a "second imaging standby mode" in which power consumption is less than that of the first imaging standby mode. In this embodiment, as the imaging standby state, either the first imaging standby mode or the second imaging standby mode is selectable, and either one of the two modes is selectable.

The first imaging standby mode is the imaging standby state in which every driving unit used in the series of imaging operations is supplied power, except the signal reading circuit 17, capable of rapid start up to the imaging ready state, allowing smooth transition to the imaging operation. Particularly, it is the state in which power is supplied to the units such as the scan drive circuit 16, photodiodes 152, TFTs 153, image memory 18, communication unit 24, and control device 28.

The second imaging standby mode is the imaging standby state in which only the image memory 18, associated with storing image, and the communication unit 24, associated with transmission of image information to outer device and receiving signal from the outer device, and control device 28 are supplied with power. In addition, at least one portion of the unit other than the above mentioned units is supplied with power less than the normal state, being an imaging standby state with a lower power consumption compared to the first imaging standby mode. As the optimum embodiment, a second imaging standby mode has power supplied only to image memory 18, communication unit 24, and control device 28, that is, a very low power consumption state that cannot perform imaging operation immediately.

The imaging stop state is the utmost power-saving state in which power supply to every driving unit of the radiographic image detection device 5 is stopped.

The input operation unit 26, as a basic state setting means for selectively setting a basic state, can set a state of operation of the radiographic image detection device 5 to any of the imaging ready state and the respective imaging standby modes. Here, the "basic state" means a state of operation selected as long as settings are not changed. For example, in case that the radiographic image detection device 5 is used under less frequent imaging operations, the second imaging standby mode would be selectively set as the basic state, because this mode allows protecting the components, such as the photodiodes 152 and the TFTs 153, which deteriorate within time elapse during power supply, and the power consumption is reduced. On the other hand, in case that the radiographic image detection device 5 is used under more frequent imaging operations, the imaging ready state or the first imaging standby mode would be selectively set as a basic state to supply the power to the photodiodes 152 and the TFTs 153 that need longer start up time, allowing rapid and effective imaging to be performed.

In the radiographic image detection device 5 of the embodiment, power is supplied to the units driven by the rechargeable battery 21. Therefore, it is preferable that the first imaging standby mode be selectively set as the basic state so as to realize a rapid and effective imaging operation with the power consumption being saved. On the contrary, in case that the imaging operation is not planned for the time being, the imaging stop state may be selected as the basic state.

Further, the input operation unit 26, a post-state setting means for selectively setting a post-state, can selectively set the state of operation of the radiographic image detection device 5 after charging the rechargeable battery 21, to the imaging ready state, either of the imaging standby modes, or the imaging stop state. The "post-state" means a state after the rechargeable battery 21 is charged. By arbitrarily setting the post state, a suitable state of operation can be selected depending on conditions whether the imaging operation is planned or not just after the charging of the battery 21, or to time slot for the charging to be performed.

Note that contents which can be input from the input operation unit 26 are not limited to selectively setting the state of operation, and otherwise the operator such as a radiologist may input and set the imaging condition, identification information of the patient, and the like.

Figure 5:
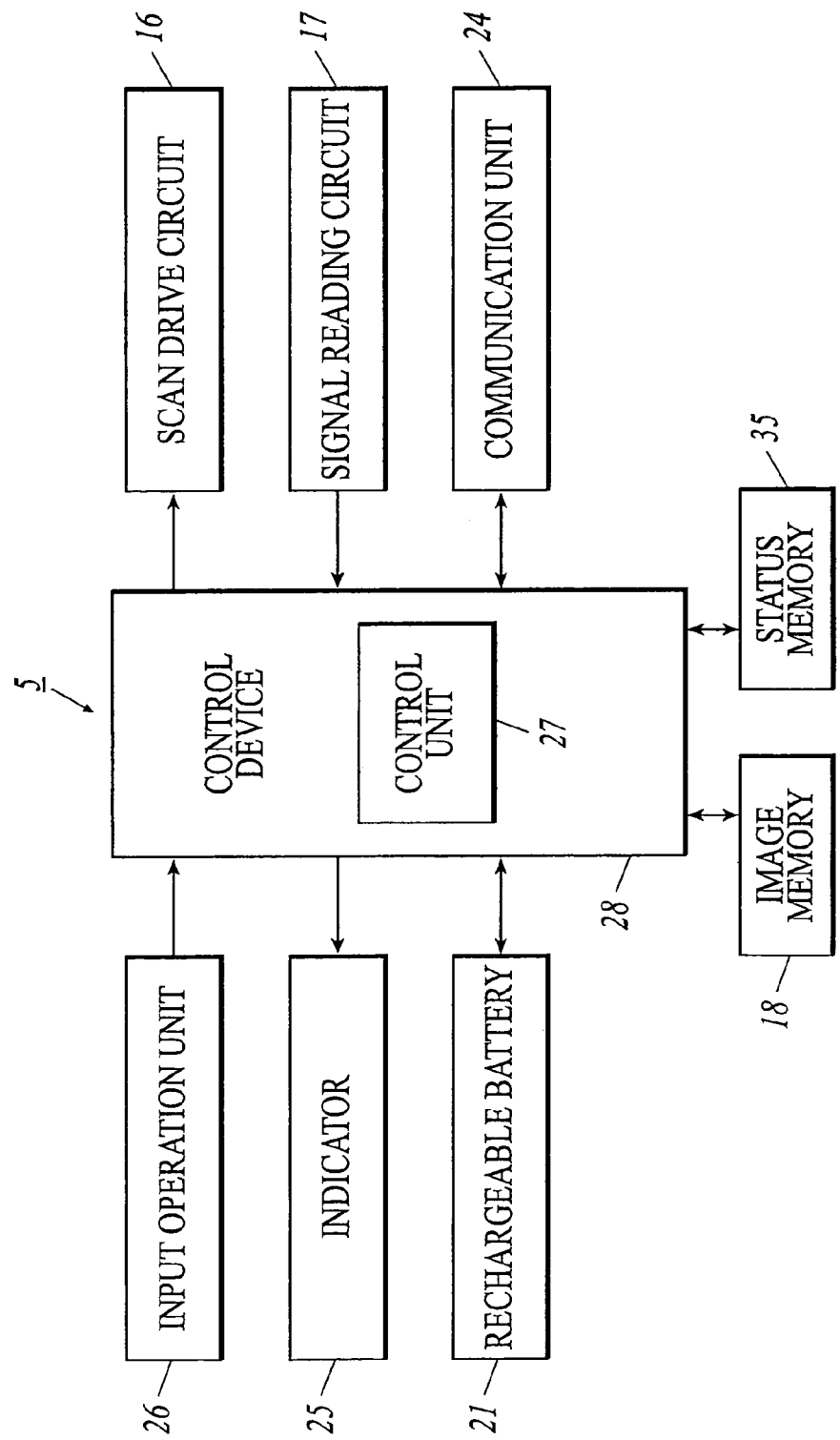
FIG. 5 is a block diagram showing a configuration of main units of the radiographic image detection device.

Description on functional configuration of radiographic image detection device will be given using FIG. 5.

The radiographic image detection device 5 includes a control device 28 provided with the control unit 27 having, for example, a general-purpose CPU, ROM, RAM and the like (none of them are shown). The control unit 27 reads predetermined programs stored in the ROM to develop the programs in a work area of the RAM, and allows the CPU to execute various kinds of operations according to the programs.

The radiographic image detection device 5 is provided with a charge quantity detecting means (not shown), which sends to the control unit 27 a signal indicating a charge status of the rechargeable battery 21, such as the voltage value of the rechargeable battery 21. The control unit 27 then has the indicator 25 display the charge quantity of the rechargeable battery 21 and the like based on the sent signal. The charge quantity detecting means may be a means in which the control unit 27 detects the charge quantity from the measurement result of a voltmeter that measures the voltage between the two electrodes, a means in which other unit independent from the control unit 27 detects the charge quantity from the measurement result of a voltmeter that measures the voltage between the two electrodes, a means in which the charge quantity is speculated from the voltage supplied, measured as the voltage supplied from the rechargeable battery 21 to the unit driven by the power (for example, control unit 27), or other form of means.

If the control unit 27 judges, based on the detected result by the charge quantity detecting means, that the battery 21 has to be charged since the charge quantity of the battery 21 is less than the predetermined level, the control unit 27 sends a signal of the judgment to the console 6 via the communication unit 24. Further, if the control unit 27 judges, based on the detected result by the charge quantity detecting means, that charging of the battery 21 has been completed, the control unit 27 sends a signal of the judgment to the console 6 via the communication unit 24. Here, the charge quantity of the battery 21 may be sent to the console 6 via the communication unit 24 steadily.

Additionally, the control unit 27 sends the current state of the radiographic image detection device 5 to the console 6 via the communication unit 24 steadily.

Additionally, status memory 35 stores the information of operation concerning the state of operation of the radiographic image detection device 5 after end of charging or replacing the rechargeable battery 21. The status memory 35 comprising a rewritable dedicated memory, such as a flash memory.

In the embodiment, if the state of operation (basic state or post state) of the radiographic image detection device 5 is selectively set by input operation into the input operation unit 26 by an operator, control unit 27 stores the information relating to the selectively set state of operation in the status memory 35 as the "information of operation after end". After end of charging or replacing the rechargeable battery 21, the control unit 27 controls the state of operation of the units driven by the power depending on the information of operation after end previously stored in the status memory 35. In more detail, the control unit 27 reads the information of operation after end previously stored in the status memory 35 to recognize the selectively set state of operation by an operator, and controls power supply to the units driven by the power from the rechargeable battery 21 so as to attain the recognized state of operation. Thus, the control unit 27 controls the state of operation of each driving unit.

The control unit 27 receives information input from the input operation unit 26 and signals sent through the communication unit 24, and controls each unit based on the sent signals.

Particularly in this embodiment, when there is input through the input operation unit 26 an instruction which selectively sets the imaging ready state, the first imaging standby mode, the second imaging standby mode, or the imaging stop state, the input signal is sent to the control unit 27. Then, the control unit 27 controls power supply from the rechargeable battery 21 so that the basic state and the post state after end of charging of the radiographic image detection device 5 can be set to the state of operation depending on the input signal, whereby power is properly supplied to the units of the radiographic image detection device 5,.

In the embodiment, while charging the rechargeable battery 21, the control unit 27 controls the state of operation of the units driven by the power to supply power to the image memory 18 and the communication unit 24 only, so that the radiographic image detection device 5 is in the second imaging standby mode which is a state of operation requiring the least power consumption.

Meanwhile, when the radiographic image detection device 5 is set to the second imaging standby mode as the basic state by selective setting through the input operation unit 26, and further, when the imaging ready state is selectively set as a post state, or the communication unit 24 receives an imaging start signal, which instructs to start imaging, from an external device such as the console 6, the control unit 27 may switch from the second imaging standby mode to the first imaging standby mode, and further to the imaging ready state step by step, so that the power supply from the rechargeable battery 21 can be controlled to supply necessary power to the units driven by the power. In this case, the power may be supplied to all units driven by the power used in a series of imaging operations so that the second imaging standby mode may be switched directly to the imaging ready state, not by step-by-step switching.

Further, when the first imaging standby mode is set as the basic state through the input operation unit 26, and imaging ready state is selected as a post state, or receives the imaging start signal, the control unit 27 may control the power supply from the rechargeable battery 21 so as to supply power to the units driven by the power sequentially so that the first imaging standby mode may be switched to the imaging ready state.

The control unit 27 drives the scan drive circuit 16 to send the pulses to the respective photoelectric conversion elements, thus scanning and driving the respective photoelectric conversion elements. Then, the image signal is read by the signal reading circuit 17 which reads the electric energy stored in the respective photoelectric conversion elements, and the read image signal is sent to the control unit 27. The control unit 27 stores the sent image signal in the image memory 18. The image signal stored in the image memory 18 is appropriately sent through the communication unit 24 to the console 6.

Figure 6:
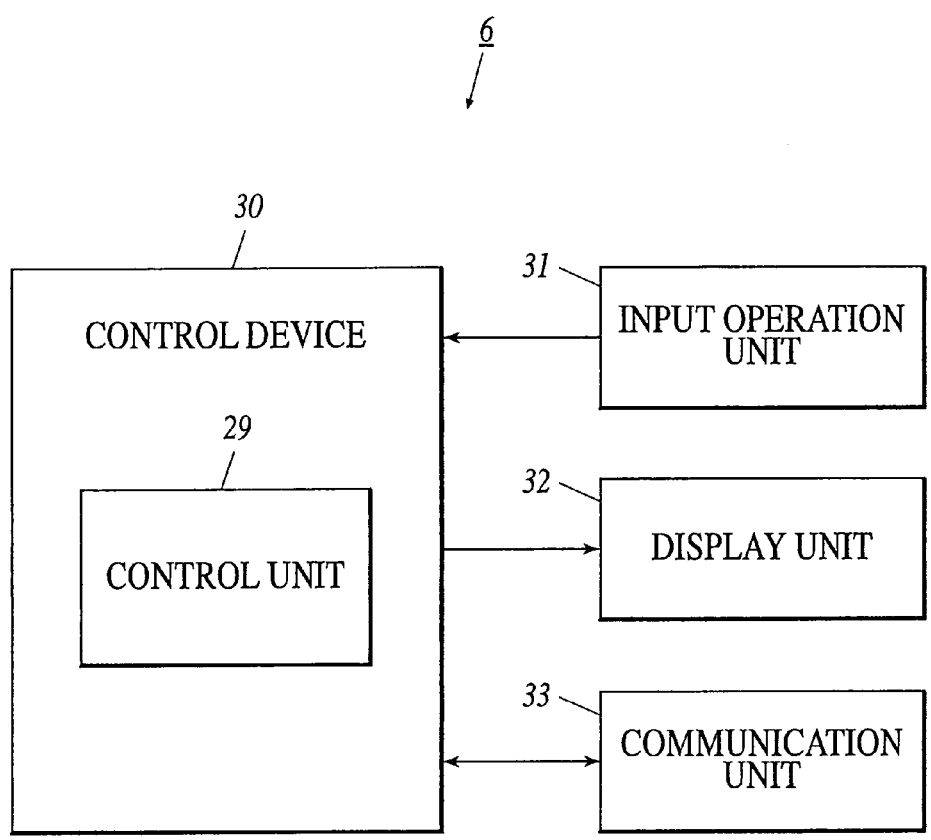
FIG. 6 is a block diagram showing a configuration of main units of a console.

Description on functional configuration of console 6 will be given using FIG. 6.

Console 6 includes a control device 30 having a control unit 29 which includes, for example, a general-purpose CPU, ROM, RAM and the like (none of them are shown). The control unit 29 reads predetermined programs stored in the ROM to develop the programs into a work area of the RAM, and allows the CPU to execute various kinds of operations according to the programs.

Further, the console 6 includes an input operation unit 31 for inputting various types of instructions and the like, a display unit 32 for displaying an image or various messages and the like, and a communication unit 33 for sending and receiving signals to and from an external device such as the radiographic image detection device 5.

The input operation unit 31 includes, for example, an operation panel, a keyboard, a mouse and the like, and a press signal sent from a key depressed on the operation panel or keyboard, and an operation signal sent from the mouse, are outputted as input signals to the control unit 29.

The display unit 32 includes, for example, a CRT (Cathode Ray Tube), and an LCD (Liquid Crystal Display), and according to an instruction signals for display from the control unit 29, displays radiographic images such as thumbnail images, and various information such as various information input from the input operation unit 31.

In the embodiment, the display unit 32 displays, in addition to the radiographic image information, various information, such as the charge quantity of the rechargeable battery 21 of the radiographic image detection device 5, whether charging of the rechargeable battery 21 has been completed, and state of operation of the radiographic image detection device 5, which are sent through the communication unit 24 of the radiographic image detection device 5. Here, the contents to be displayed on the display unit 32 are not limited to those described above, and more information may be displayed. Alternatively, all items described above may be not displayed and at least one or more items of these may be displayed.

The communication unit 33 communicates various types of information with the radiographic image detection device 5 through the base station 4 by a wireless communication system such as a wireless LAN.

A signal input from the input operation unit 31, a signal received from the outer device through the communication unit 33, and the like are sent to the control unit 29. The control unit 29 obtains a thumbnail image, a radiographic image desired by a doctor, and the like, for example, by executing predetermined image process based on the radiographic image information detected by the radiographic image detection device 5.

Figure 7A:
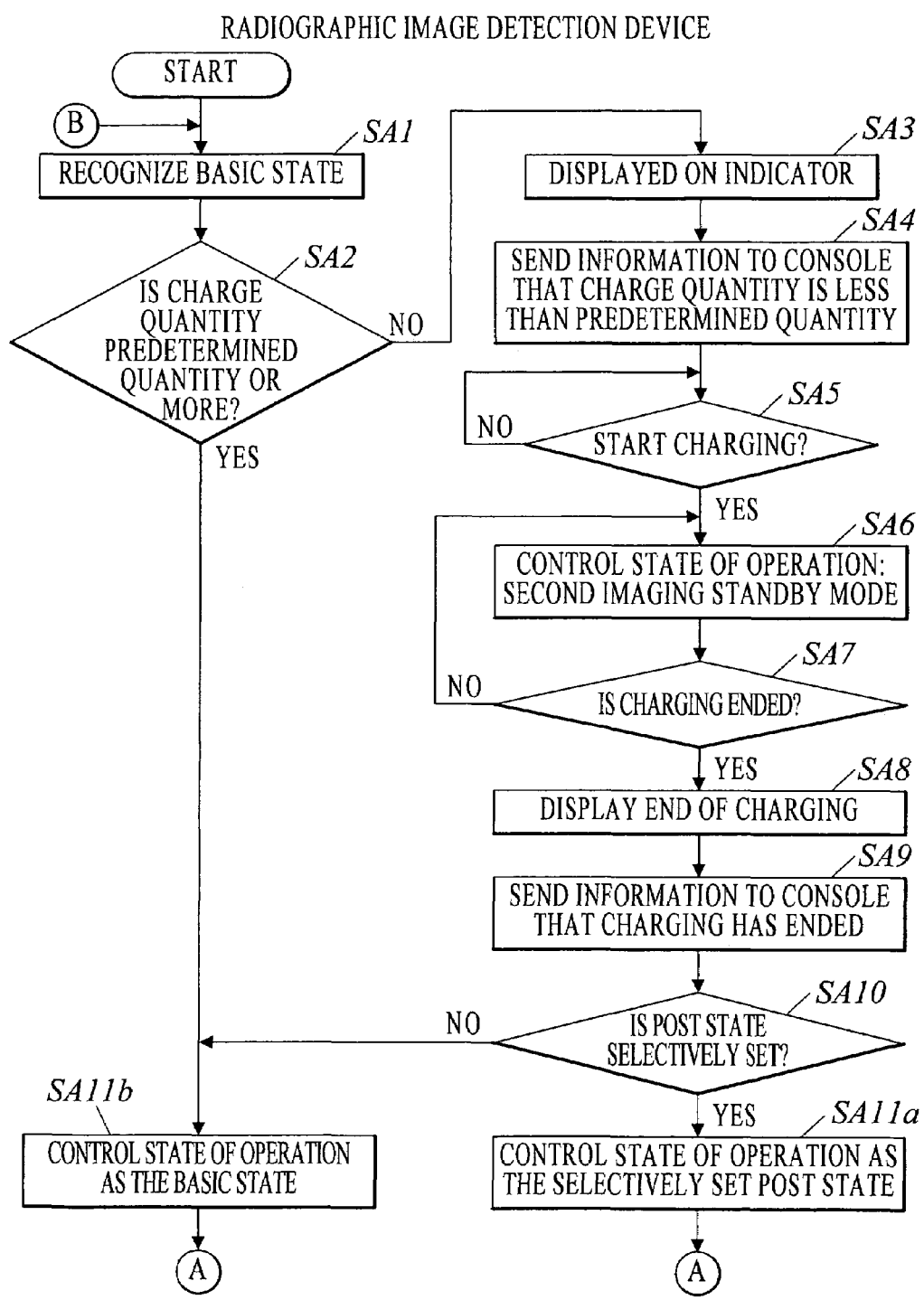
FIGS. 7A and 7B are flow charts showing operations in time sequence executed in the radiographic image detection device when the radiographic imaging system runs.
Figure 7B:
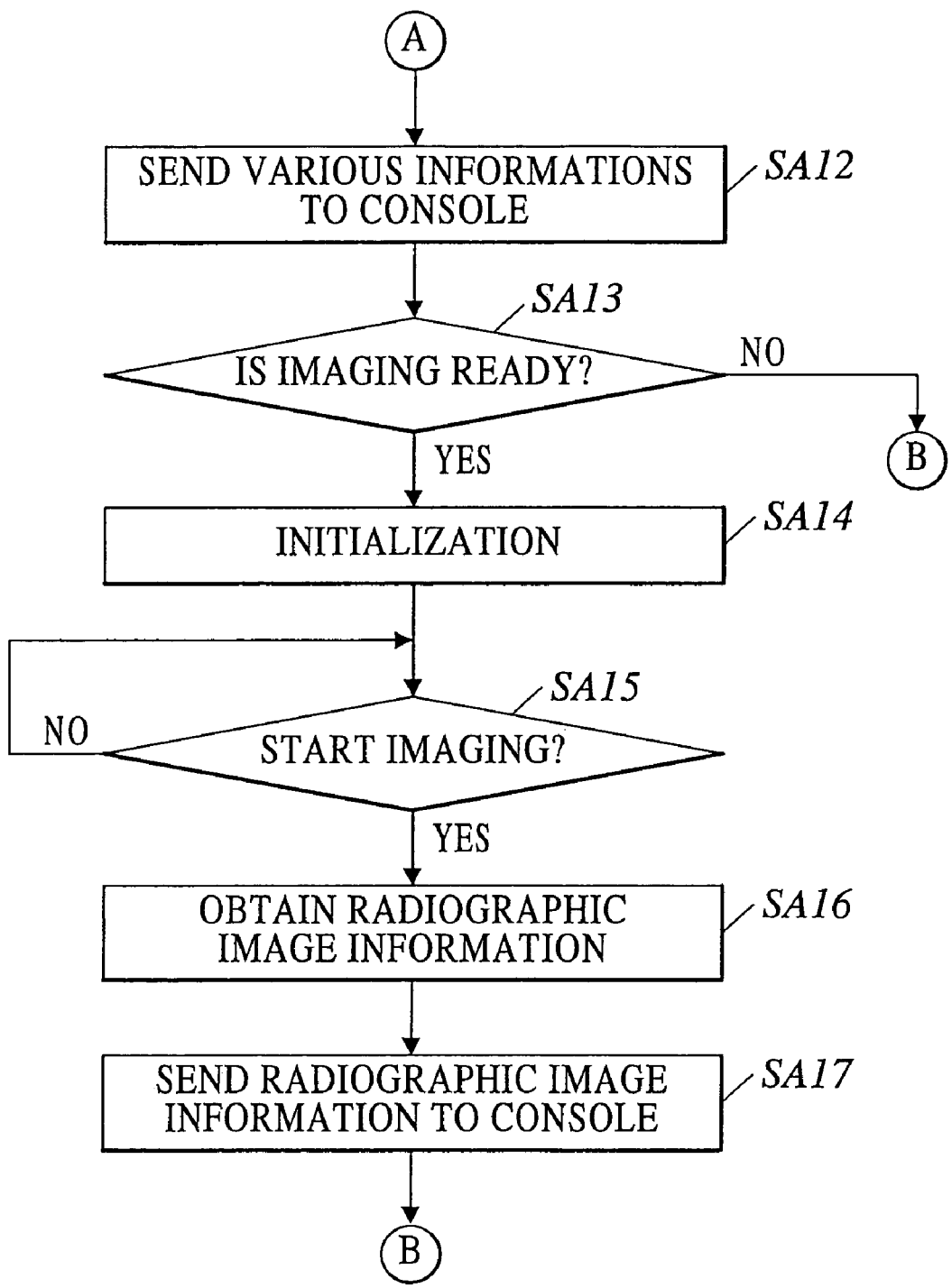
Figure 8:
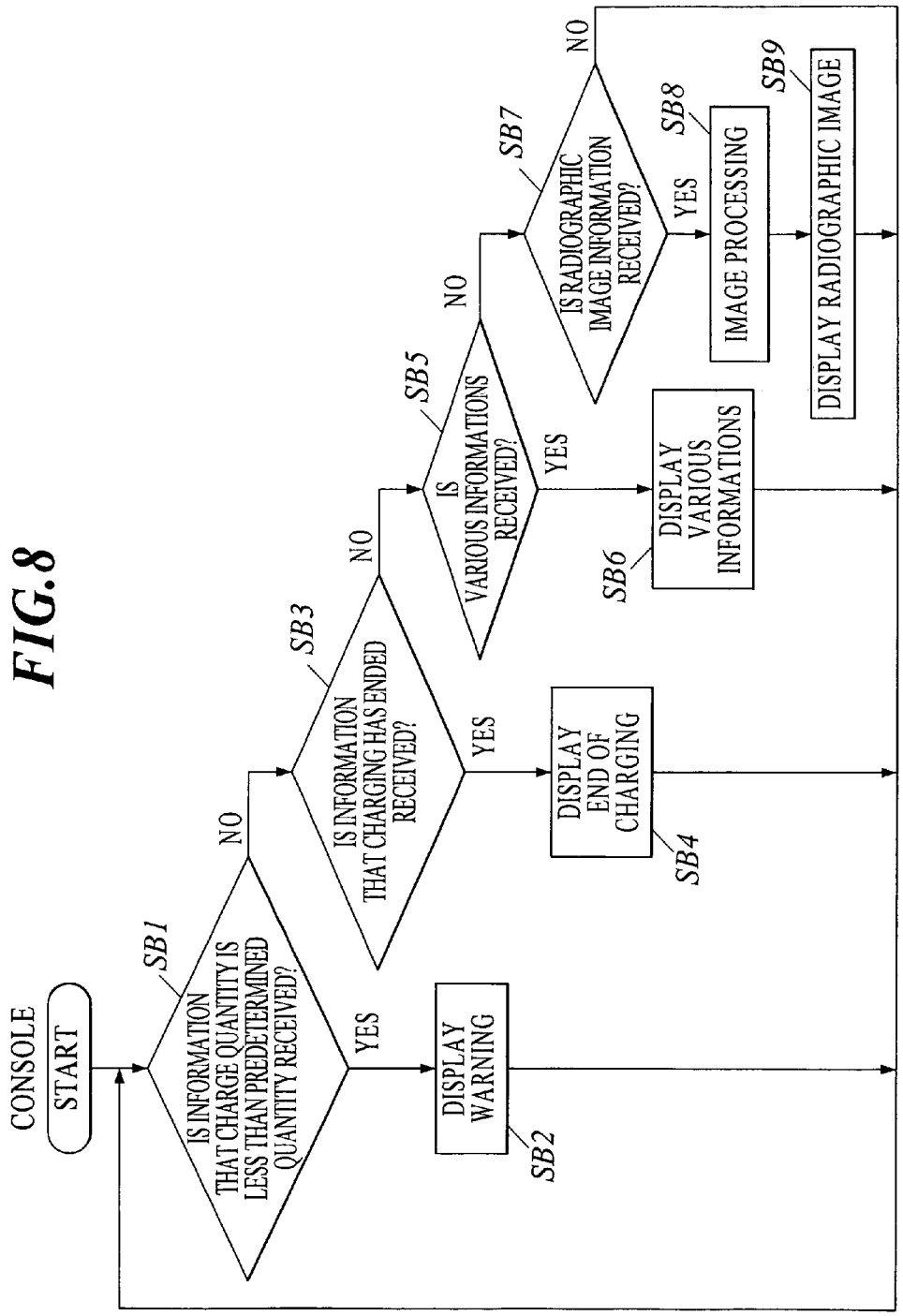
FIG. 8 is flow chart showing operations in time sequence executed in the console when the radiographic imaging system runs.

A description will now be given on the mechanism of the radiographic imaging system 1 according to the embodiment with reference to FIGS. 7a, 7b, and 8. (Description will be given separately for operations at radiographic image detection device 5 (with reference to FIGS. 7a and 7b) and operation at console 6 (with reference to FIG. 8)).

Initially, in the state that the basic state of the radiographic image detection device 5 is selectively set, the control unit 27 recognizes from the information of operation stored in the status memory 35, which among the imaging ready state, the imaging standby state or the imaging stop state is selectively set as the basic state (step SA1).

After recognizing the basic state, the control unit 27 has the charge quantity detecting means detect charge quantity of the rechargeable battery 21, and judges whether the charge quantity of the rechargeable battery 21 is the predetermined charge quantity or more necessary for imaging and the like (step SA2). If judged that the charge quantity of the rechargeable battery 21 is predetermined charge quantity or more (step SA2; YES), the state of operation of the units driven by the power is controlled according to the recognized basic state (step SA11b, refer to later description).

On the other hand, in step SA2, if judged that the charge quantity of the rechargeable battery 21 is less than the predetermined charge quantity (step SA2; NO), the control unit 27 has the indicator 25 display that the charge quantity of the rechargeable battery 21 is less than the predetermined charge quantity (step SA3), and also sends a signal indicating the judgment to the console 6 (step SA4).

Subsequently, control unit 27 repeatedly judges whether charging of rechargeable battery 21 has been initiated through the detection result from the charge quantity detection means (step SA5). If it is judged that the operator has initiated charging of the rechargeable battery 21 (step SA5; YES), the operation will move on to step SA6. In this case, when the operator performs charging of the rechargeable battery (place radiographic image detection device 5 on the charging device 23) depending on the warning on display 25, the terminals of the charging device 23 are connected to the terminals 22 of the radiographic image detector 5 to start charging the rechargeable battery 21.

While charging, the control unit 27 controls the state of operation of the units driven by the power from the rechargeable battery 21 to image memory 18 and communication unit 24 only, so that the radiographic image detection device 5 is in the second imaging standby mode which has the least power consumption (step SA6).

In this state, the control unit 27 has the charge quantity detecting means detect the quantity of charge of the rechargeable battery 21, and repeatedly judges whether the quantity of charge of the rechargeable battery 21 has reached the predetermined charge quantity and the charging has been completed (step SA7). If judged that the charging of the rechargeable battery 21 has been completed (step SA7; YES), the control unit 27 allows the indicator 25 to display the end of charging (step SA8), and also send a signal of the judgment to the console 6 (step SA9).

When the charging of the rechargeable battery 21 has been completed, the control unit 27 judges whether the post state of the radiographic image detection device 5 is selectively set by the operator (step SA10). Selective setting of the post state of the radiographic image detection device 5 is an operation permitted at any time so long as it is performed prior to operation step SA10, and it may be performed before charging the rechargeable battery 21 starts, in the middle of charging the rechargeable battery 21, or after end of charging the rechargeable battery 21. When selective setting of the post state of the radiographic image detection device 5 is operated, the post state is stored in the status memory 35 as running information after end of charging.

If the control unit 27 judges as a result of the judgment that the post state is selectively set (step SA10; YES), the control unit 27 recognizes the selectively set post state based on the running-information-after-end stored in the status memory 35, and allows each part to be powered from the rechargeable battery 21 so as to be in the recognized post state (step SA11a). On the other hand, if judged that the post state is not selectively set (step SA10; NO), the control unit 27 recognizes the selectively set basic state based on the running-information-after-end stored in the status memory 35, and controls the state of operation of the units driven by the power so that each unit is powered from the rechargeable battery 21 to be in the recognized basic state (step SA11b).

In other words, if the imaging ready state is selectively set as the basic state or the post state, the control unit 27 supplies power from the rechargeable battery 21 to all units driven by the power used in the series of imaging operation. If the first imaging standby mode of the imaging standby state is selectively set as the basic state or the post state, the control unit 27 supplies power from the rechargeable battery 21 to respective units driven by the power such as the scan drive circuit 16, photodiodes 152, TFTs 153, image memory 18 and communication unit 24. If the second standby mode of the imaging standby state is selectively set as the basic state or the post state, the control unit 27 supplies power from the rechargeable battery 21 to the image memory 18 and the communication unit 24. If the imaging stop state is selectively set as the basic state or the post state, the control unit 27 does not supply power from the rechargeable battery 21 to any unit.

Alternatively, the console 6 may have the configuration provided with status memory 35, and depending on the input operation from the input operation unit 31 of the console 6, may store the information of operation after end. The control unit 27 in the radiographic image detection device 5 or the control unit 29 in the console 6 may read the information of operation after end stored in the status memory 35, control unit 27 of the radiographic image detection device 5 may receive the information of operation, and depending on the received information of operation, recognize the selectively set state of operation, and control the state of operation of the units driven by the power so as to be in the recognized state of operation.

Thereafter, when the state of operation of the radiographic image detection device 5 reaches the basic state or the post state after end of charging, which is previously set selectively, the control unit 27 sends to the console 6, not only the information on the state of operation of the radiographic image detection device 5, but also various information such as charge quantity of the rechargeable battery 21 (step SA12).

Subsequently, the control unit 27 judges whether the state of operation of radiographic image detection device 5 is selectively set as the imaging ready state and the state of operation of the radiographic image detection device 5 is actually the imaging ready state (step SA13), and as a result of such judgment, the state of operation of the radiographic image detection device 5 is actually the imaging ready state (step SA13; YES), for preparation of new imaging, performs initialization operation such as resetting the stored image information and dark-image reading operation (step SA14). If it is judged that state of operation is not at an imaging ready state (step SA13; NO), the operation returns step SA1.

Subsequently, the control unit 27 repeatedly judges whether radiographic imaging has been initiated by the operator (step SA15), and as a result of such judgment, judged that radiographic imaging has been initiated (step SA15; YES), the operation will progress to step 16. When radiographic imaging starts actually, the radiation source 12 emits the radiation, and the control unit 27 operates the scan drive circuit 16 to send the pulses to each photoelectric conversion elements, thus scanning and driving the respective photoelectric conversion elements, and also reads the electric energy stored in the respective photoelectric conversion elements with the signal reading circuit 17 to obtain radiographic image information of (step SA16).

After obtaining the radiographic image information, the control unit 27 stores the radiographic image information of the subject 9 in the image memory 18, and transmits the image information to the console 6 (step SA17). Each operation described in steps SA1 through SA17 is repeated.

Continuously, within console 6, control unit 29 judges whether it received information that charge quantity of the rechargeable battery 21 is less than the predetermined amount (step SB1), through the operation of the above mentioned step SA4 by the control unit 27 of the radiographic image detection device 5. As a result of the judgment, when the control unit 29 receives information that charge quantity of the rechargeable battery 21 is less than the predetermined amount (step SB1; YES), it warns the operator by means such as displaying a message that the charge quantity is less than the predetermined amount on the display unit 32 (step SB2). Console 6 may also receive the charge quantity of the rechargeable battery 21 as a signal constantly from the radiographic image detection device 5, and the control unit 29 may display the charge quantity of the rechargeable battery 21 on the display unit 32 constantly depending on the signal received.

On the contrary, when the control unit 29 does not receive information that charge quantity of the rechargeable battery 21 is less than the predetermined amount (step SB1; NO), it judges whether it has received a message that charging of the rechargeable battery 21 has completed, depending on the operation of the mentioned step SA9 by the control unit 27 of the radiographic image detection device 5 (step SB3). As a result of the judgment, when the control unit 29 receives information that charging of the rechargeable battery 21 has completed (step SB3; YES), it displays a message that the charging of the rechargeable battery 21 has completed on the display unit 32 (step SB4).

On the other hand, when the control unit 29 judges that it has not received information that charging of the rechargeable battery 21 has completed (step SB3; NO), it judges whether it has received information concerning the state of operation of the radiographic image detection device 5, charge quantity of the rechargeable battery 21, and the like, depending on the operation of the mentioned step SA12 by the control unit 27 of the radiographic image detection device 5 (step SB5). As a result of the judgment, when the control unit 29 judges that it has received such information (step SB5; YES), it displays information concerning the state of operation of the radiographic image detection device 5, charge quantity of the rechargeable battery 21, and the like, on the display unit 32 (step SB6).

On the contrary, when the control unit 29 judges that it has-not received information concerning the state of operation of the radiographic image detection device 5, charge quantity of the rechargeable battery 21, and the like (step SB5; NO), it judges whether it has received radiographic image signal, depending on the operation of the mentioned step SA17 by the control unit 27 of the radiographic image detection device 5 (step SB7). As a result of the judgment, when the control unit 29 judges that it has received such radiographic image signal (step SB7; YES), it performs predetermined image operation (step SA8) depending on the received signal, obtain thumb-nail image and a radiographic image that a doctor and the like desire, and displays radiographic image on the display unit 32 (step SB9).

The control unit 29 repeatedly performs the mentioned serial steps SB1-SB9 when operations described in step SB2, step SB4, step SB6, and step SB9 is concluded, including when it judges that it has not received radiographic image signal (step SB7; NO).

As described above, according to the embodiment, power is supplied to each unit so that the radiographic image detection device 5 can be in the imaging ready state, imaging standby state or imaging stop state. Therefore, by stopping power supply to the photodiodes 152 and to the TFTs 153 when an imaging operation is not scheduled for a while, the photodiodes 152 and the TFTs 153 can be protected from deterioration, and the lifetime of the radiographic image detection device 5 can be made longer. Additionally in the imaging standby state and in the imaging stop state, since power is not supplied to the signal reading circuit 17 and the like which require larger power consumption, power consumption can be reduced and multiple imaging can be performed within charging once.

The radiographic image detection device 5 has two modes in the imaging standby state. In the first imaging standby mode, power supply is maintained for the photodiodes 152 and the TFTs 153 and the like, which need longer start up time if the power supply is once stopped, and power supply is stopped only for the signal reading circuit 17 that require larger power consumption. Accordingly, if the detector is set to the first imaging standby mode after end of charging or replacing the battery, the detector can move to the imaging state immediately with the power consumption held down.

On the other hand, in the second imaging standby mode, power is supplied only to minimum parts such as the communication unit 24 and the like that receives signals from the outer device, and power supply is stopped to the photodiodes 152 and the TFTs 153 and the like, which deteriorate within time elapse during power supply. Therefore, if the detector is set to the second imaging standby mode, the power consumption can be held down to minimum, the photodiodes 152 and the TFTs 153 can be protected from deterioration, and the detector can move to the imaging ready state readily by receiving a signal from the outer device when imaging operation is resumed again, thus effective imaging operation can be attained.

In the embodiment, two kinds of imaging standby modes can be selected, however, imaging standby modes are not limited to these two kinds. For example, such an imaging standby mode may be selected that power supply is stopped only to the photodiodes 152 and the TFTs 153, which deteriorate within time elapse if power is supplied. Such another imaging standby mode may be selected that power is not supplied to other parts than the image memory 18 and the communication unit 24, and that power starts being supplied earlier than other parts, only to the photodiodes 152 and the TFTs 153, which need longer start-up time if the power supply is once stopped. Additionally, a plurality of modes may be selected. Further, only either of the two imaging standby modes exemplified in the embodiment may be installed.

In the embodiment, the input operation unit 26 is configured, as for a selectively setting means, to switch and selectively set the imaging ready state, various imaging-standby state, or the imaging stop state, but a selectively setting means may be provided separately from the input operation unit 26.

The selectively setting means is not limited to the case that it is provided within the radiographic image detection device 5, and, for example, the input operation unit 31 of the console 6 may be functioned as a selectively setting means. That is, the input operation unit 31 may set the basic state of the radiographic image detection device 5 as a basic state setting means, and set the state of operation after charging as a post-state setting means. Alternatively, the charging device 23 or the like may be provided with a selectively setting means, and may function as a post-state setting means for setting a post state after end of charging.

The radiographic image detection device 5 in the embodiment has the input operation unit 26 on the outside of the housing 14, which the operator such as a radiologist, input and set imaging conditions, identification information of a patient, and various kinds of instructions. However, as described above, if the selective setting means is provided separately from a means for inputting imaging conditions or the like, or if input means other than the input operation unit 26 of the radiographic image detection device 5, such as the input operation unit 31 of the console 6, functions as a selective setting means, the radiographic image detection device 5 may not be provided with the input operation unit 26.

In the embodiment, both the basic state setting means that selectively sets the basic state and the post-state setting means that selectively sets the post state are provided as selectively setting means, but either one of the two selectively setting means, the basic state setting means or the post-state setting means, may be provided as a selective setting means.

Further, the selectively setting means may automatically switch the state of operation of the radiographic image detection device 5 after end of charging or replacement depending on which time slot of the day charging or replacing the battery 21 is carried out. For example, if the charging or replacement is performed in the daytime, it is possible that next imaging is operated immediately after end of charging or replacement, and if performed at night, it is possible that next imaging is not operated for the time being. In other words, the running sate may be set as such, if charging or replacing of the battery 21 is carried out in time from 6 a.m. to 6 p.m., it will be in the imaging ready state or the first imaging standby mode after end of charging or replacement, and if carried out in time from 6 p.m. to 6 a.m., it will be in the second standby mode or the imaging stop state after end of charging or replacement.

In the embodiment, the rechargeable battery 21 is provided as the power supply, however, the power supply is not limited to this example. For example, there may be provided, instead of the rechargeable battery 21, a replaceable and disposable battery, such as a manganese battery, an alkaline battery, an alkaline button battery, a lithium battery, a silver oxide battery, an air-zinc battery, a nickel-cadmium battery, a mercury battery, and a lead battery.

Further, the rechargeable battery 21 may be detachable mounted on the housing 14 and there may be provided a turning-off mechanism in which power is not supplied to the units driven by the power from the battery 21 (turned-off state) at the time of detaching/attaching the battery 21.

Figure 9:
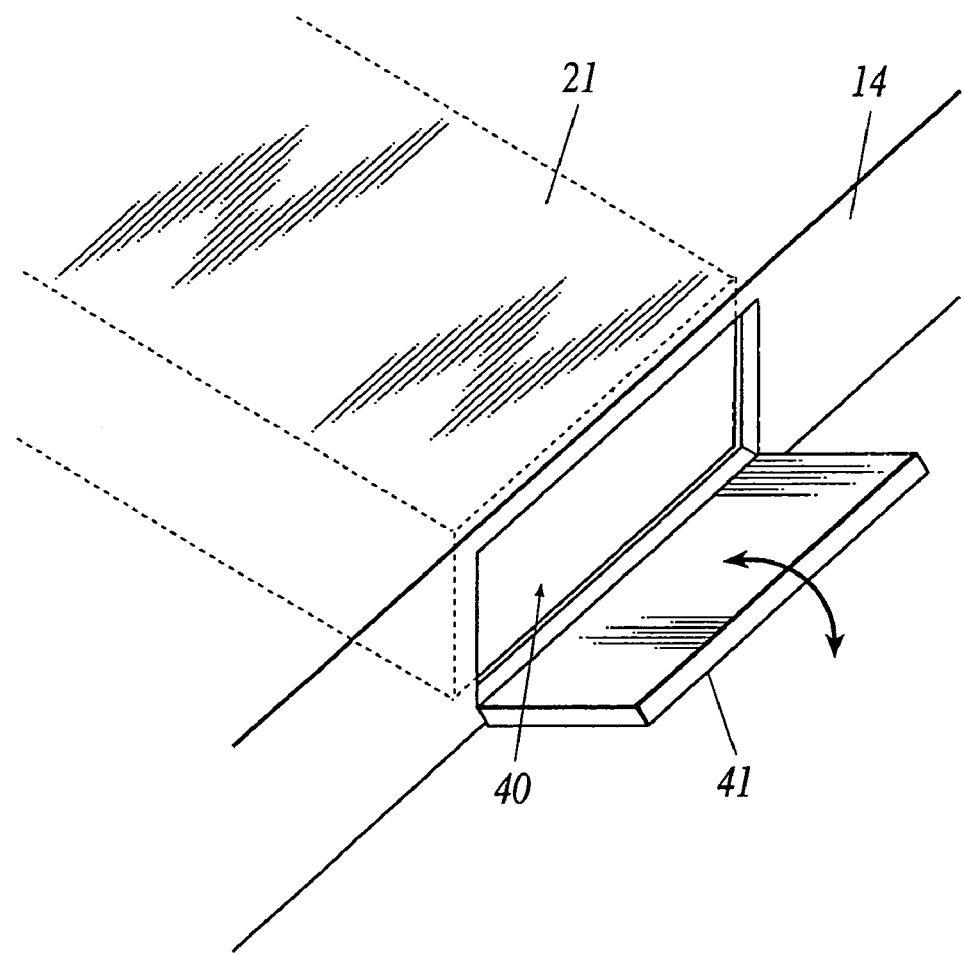
FIG. 9 illustrates one example of a turning-off mechanism.

One example of the turning-off mechanism is shown in FIG. 9. As shown in FIG.9, the turning-off mechanism has an opening 40 formed on the housing 14, the opening 40 having a rectangular shape and a size of the rechargeable battery 21 to be inserted, and a lid 41, capable of covering the opening 40, is connected with the housing 14 via a hinge (not shown). The lid 41 can be freely opened and closed against the opening 40, and the rechargeable battery 21 can be replaced with another rechargeable battery 21 when the lid 41 opened.

In the turning-off mechanism, turning on/off of the rechargeable battery 21 is in conjunction with opening/closing movement of the lid 41. That is, when the lid 41 is opened, an electric circuit between the rechargeable battery 21 and the control unit 27 is shut off, and power is not supplied to the units driven by the power from the rechargeable battery 21 (turned-off state). To the contrary, when the lid 41 covers the opening 40, the electric circuit between the rechargeable battery 21 and the control unit 27 is connected, and power can be supplied to the units driven by the power from the rechargeable battery 21 (turned-on state).

Meanwhile, in case that a replaceable and disposable or rechargeable battery 21 is used as a power source, for example, while an operator is taking out the disposable or rechargeable battery 21 for replacement from the radiographic image detection device 5, the detection device 5 is turned off, and when it detects that the rechargeable battery 21 is attached to the radiographic image detection device 5 after end of replacing the battery, the detection device 5 moves to a state of operation set as the post state. At this time, if the imaging stop state is set as the post state by the selectively setting means, the radiographic image detection device 5 remains in the imaging stop state after the replacement of the battery 21 has completed and the rechargeable battery 21 is attached to the detection device 5.

In this case, a sensor or a mechanical switch or the like may be provided, on a contacting portion of the battery or a lid of a holding part to hold the battery, for detecting whether the battery is taken out or placed, and sending a signal to the control unit 27 for judgment. Further, there may be provided a switch on the housing 14 for turning on/off the power, and the power may be turned off within operation of this switch. Further, the power may be turned on/off with a signal from the console 6 or the like. Meanwhile, in case that the radiographic image detection device 5 is turned off during replacement of the battery as described above, the detection device 5 moves to a state of operation set as the post state upon end of the battery replacement. When the post state is not particularly set, the detection device 5 may move to a state of operation previously set as the basic state.

Further, in case that the replaceable battery or the replaceable and rechargeable battery 21 is used, there may be provided an auxiliary power supply other than the battery. If the auxiliary power supply is provided, the detection device 5 is, during battery replacement, in the second standby mode that is a state of operation requiring the least power consumption, and moves to a state of operation set as the post state after end of battery replacement. In this case, when the post state is not particularly set, the detection device 5 may also move to a state of operation previously set as the basic state. As described above, by providing an auxiliary power supply other than the replaceable battery or the replaceable and rechargeable battery 21, at least minimum power required can be supplied to the radiographic image detection device 5 during replacement of the battery or the rechargeable battery 21. Accordingly, it can be prevented that the image information stored in the image memory 18 is erroneously deleted, and that the detection device falls in a state in which a signal from an external device, such as the console 6, cannot be received.

In the embodiment, the radiographic image detection device 5 is, while charging the rechargeable battery 21, in the second imaging standby mode in which power is supplied from the rechargeable battery 21 to the image memory 18 and the communication unit 24 only, however, the state of operation of the detection device 5, while charging the rechargeable battery 21, is not limited to this case. It is preferable for the detection device 5 to be in a state of operation requiring less power consumption while charging the rechargeable battery 21, and particularly to be in a state of operation that requires minimum power consumption, in which power is supplied only to the units driven by the power that need power supply at the least.

However, for example, taking operation conditions into consideration, the detection device may be set to be in the first imaging standby mode during charging.

In addition, if it is considered preferable to maintain the state of operation before charging for operation conditions reasons, for example, the detection device may maintain the state of operation before charging during charging, too.

Alternatively, the detection device, during charging, may be set to be in a state of operation set as the post state. That is, when charging starts, the state of operation of the radiographic image detection device 5 may be switched to a state of operation set as the post state, and charging may be carried out with the state of operation maintained.

Further, if the imaging stop state is selected as the post state, the detection device may be set to the imaging stop state while charging.

If the charging is carried out by placing the radiographic image detection device 5 on the charging device 23, such as a cradle, the charging device 23 may selectively set the state of operation of the detection device 5 during charging. Alternatively, the console 6 or the like may set the state of operation of the detection device 5 during charging.

Meanwhile, as described above, if a replaceable battery or replaceable and rechargeable battery is provided as the power supply source and power can be supplied from an auxiliary power supply during the battery replacement, the state of operation of the detection device 5 during the battery replacement is, similarly, not limited to the second imaging standby mode.

A charging device such as a cradle is used for charging the rechargeable battery 21 in the embodiment, or otherwise by connecting the terminals of the radiographic image detection device with a cord, an external power supply may supply the power to charge the battery. Further, the rechargeable battery may be charged in the condition where it is taken out of the radiographic image detection device.

In the embodiment, power is supplied to each driving unit from the rechargeable battery 21 during and after charging. However, during and after charging, if the radiographic image detection device 5 is placed on the charging device 23 such as a cradle connected to an external power supply (not shown), or if the charging terminals 22 are connected with an external power supply through a cord as described above, the external power supply may supply power to the units.

In the embodiment, the radiographic imaging device 10 is operated by the radiographing operation device 3, otherwise, the radiographic imaging device 10 may be operated by the console 6 or the like. In this case, the radiographing operation device 3 is not needed, and the system configuration can be simplified.

In the embodiment, the control unit 27 controls not only power supply from the rechargeable battery 21, but also all units driven by the power, such as the scan drive circuit 16, the signal reading circuit 17, the communication unit 24, and the like. However, the power supply from the rechargeable battery 21 and units driven by the power of the radiographic image detection device 5, such as the scan drive circuit 16, the signal reading circuit 17, the communication unit 24, and the like, may be controlled by respective separate controllers.

Second Embodiment

Next, another embodiment of the invention will be described. The second embodiment is a modification of the first embodiment, and points different from the first embodiment will be described below.

In the present embodiment, the radiographic image detection device 5 has, as the state of operation, the imaging ready state and the imaging standby state similar to the above description, and the state of operation can be previously switched and set by operating the input operation unit 26.

The state of operation of the radiographic image detection device 5 can be selectively set by the input operation unit 26 or an external device, such as the console 6 or the like. Additionally, the state of operation may be previously set so as to be automatically switched depending on time elapsed after imaging. That is, the detector may move to the first imaging standby mode after a certain time elapsed after the imaging, and may further move to the second imaging standby mode after a certain time elapsed under the first imaging standby mode. Further, the state of operation of the radiographic image detection device 5 may be automatically switched, for example, depending on the time slot of the day. That is, it is possible that continuous imaging operations are performed in the daytime while it is possible that imaging is not performed for the time being at night. Accordingly, the state of operation may be previously set such that the detector may be in the first imaging standby mode from 6 a.m. to 6 p.m. and before imaging starts, and may be in the second standby mode from 6 p.m. to 6 a.m.

It is appropriately sent by the control unit 27 to the console 6 through the communication unit 24, in which state of operation the radiographic image detection device 5 is, among the above-described states of operation.

The radiographic image detection device 5 stores in the state memory 35, as the information of operation after end, information on the state of operation just before charging the rechargeable battery 21 in the radiographic image detection device 5. The state of operation of the detection device 5 is stored, as information, in the RAM or the like of the control unit 27 as needed, and when the terminals 22 of the detection device 5 is connected to the terminals of the charging device 23 to start charging the rechargeable battery 21, the information on the state of operation just before charging the rechargeable battery 21 in the detection device 5, which is stored in the RAM, is stored into the status memory 35, as the information of operation after end.

If the control unit 27 judges that charging of the rechargeable battery 21 has completed based on the detected result from the charge quantity detecting means, the control unit 27 reads from the status memory 35 the information of operation after end indicating the state of operation just before charging the rechargeable battery 21 in the radiographic image detection device 5, recognizes the state of operation just before charging the rechargeable battery 21 in the detection device 5, supplies power from the rechargeable battery 21 to each driving unit of the detection device 5 so as to be in the same state of operation as the recognized state of operation, and thus controls the state of operation of each driving unit.

Figure 10B:
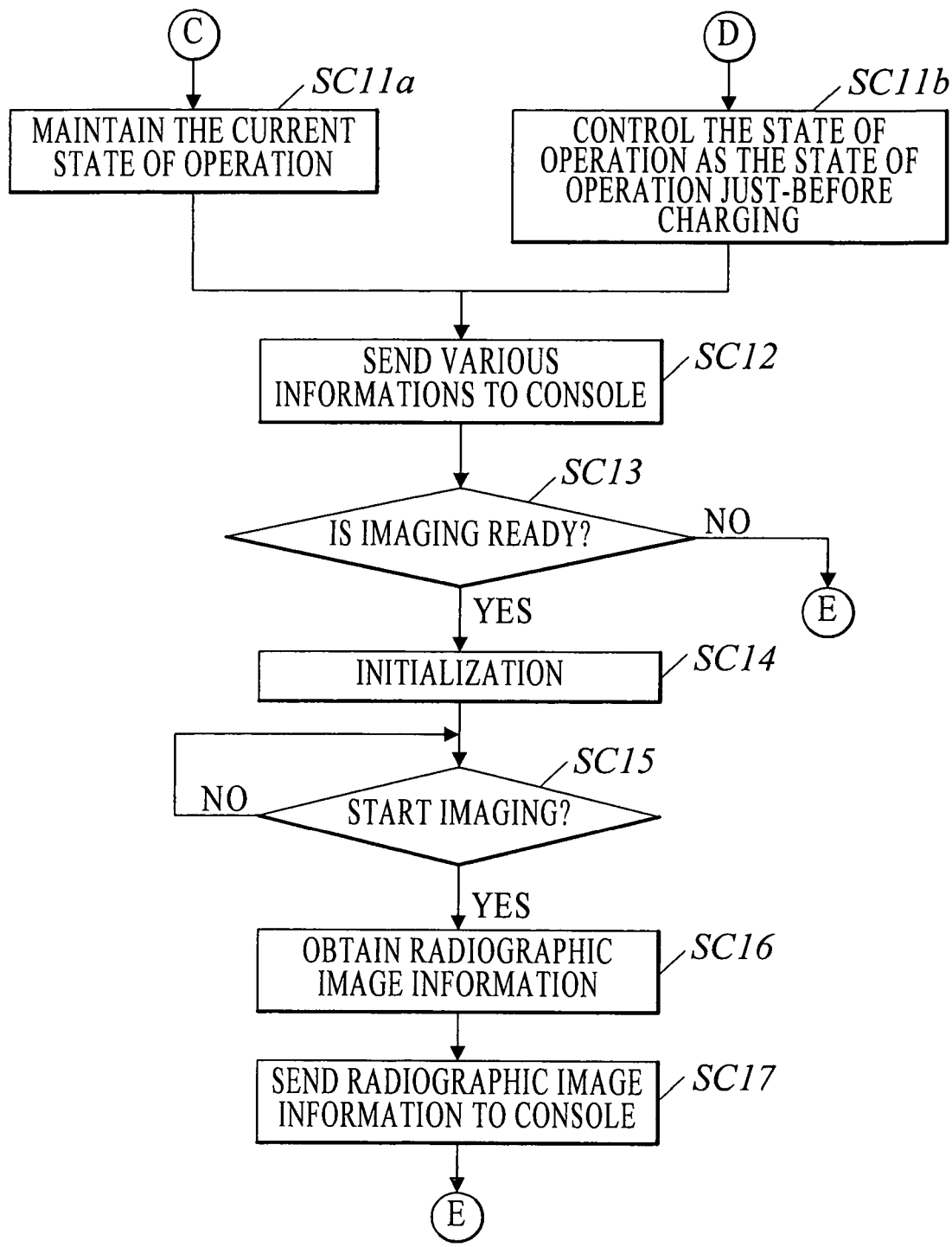

A description will now be given on the mechanism of the radiographic imaging system 1 according to the embodiment with reference to FIGS. 10a, 10b, and 11. (Description will be given separately for operation at radiographic image detection device 5 (with reference to FIGS. 10a and 10b) and operation at console 6 (with reference to FIG. 11)).

Initially, in a state that the state of operation of the radiographic image detection device 5 is stored, as information, in the RAM of the control unit 27, the control unit 27 has the charge quantity detecting means detect the charge quantity of the rechargeable battery 21, and judges whether the charge quantity is predetermined quantity or more necessary for imaging and the like (step SC1). As a result of judgment, if judged that the charge quantity of the rechargeable battery 21 is predetermined quantity or more, the control unit 27 controls the state of operation of each driving unit depending on the stored state of operation (step SC11a, refer to a later description).

On the other hand, if judged that the charge quantity of the rechargeable battery 21 is less than the predetermined charge quantity (step SC1; NO), the control unit 27 has the indicator 25 display the state that the charge quantity of the rechargeable battery 21 is less than the predetermined charge quantity (step SC2), and also sends a signal indicating the fact to the console 6 (step SC3).

Subsequently, control unit 27 repeatedly judges whether charging of rechargeable battery 21 has been initiated through the detection result from the charge quantity detection means (step SC4). If it is judged that the operator has initiated charging of the rechargeable battery 21 (step SC4; YES), the operation will move on to step SC5. In this case, when the operator performs charging of the rechargeable battery (place radiographic image detection device 5 on the charging device 23) depending on the warning on display 25, the terminals of the charging device 23 are connected to the terminals 22 of the radiographic image detector 5 to start charging the rechargeable battery 21.

When charging of the rechargeable battery 21 starts, the control unit 27 stores in the status memory 35 the information on the state of operation of radiographic image detection device 5 (state of operation just before charging the rechargeable battery 21) as information on the state of operation after end, which is stored in the RAM (step SC5).

While charging, the control unit 27 controls the state of operation of each driving unit so that the radiographic image detection device 5 may be in the second imaging standby mode, which is a state of operation requiring the minimum power consumption, by supplying power from the rechargeable battery 21 only to the image memory 18 and the communication unit 24 (step SC6).

In this state, the control unit 27 has the charge quantity detecting means detect the charge quantity of the rechargeable battery 21, and repeatedly judges whether the charge quantity of the rechargeable battery 21 has reached the predetermined charge quantity and the charging has been completed (step SC7). If judged that the charging of the rechargeable battery 21 has been completed (step SC7; YES), the control unit 27 allows the indicator 25 to display the state (step SC8), and also sends a signal of the state to the console 6 (step SC9).

When the charging of the rechargeable battery 21 has been completed, the control unit 27 reads from the status memory 35 the information of operation after end indicating the state of operation just-before charging the rechargeable battery 21 in the detection device 5, recognizes the state of operation just-before charging the rechargeable battery 21 in the detection device 5 (step SC10), supplies necessary power from the rechargeable battery 21 to each driving unit of the detection device 5 so as to be in the same state of operation as the recognized state of operation, and thus controls the state of operation of each driving unit (step SC11b).

That is, if the state of operation just-before charging the detection device 5 is the imaging ready state, the control unit 27 supplies power from the rechargeable battery 21 to all units driven by the power used in the series of imaging operation. If the state of operation just-before charging in the detection device 5 is the first imaging standby mode, the control unit 27 allows supplying power from the rechargeable battery 21 to respective units driven by the power such as the scan drive circuit 16, photodiodes 152, TFTs 153, image memory 18 and communication unit 24. If the state of operation just-before charging the detection device 5 is the second standby mode, the control unit 27 supplies power from the rechargeable battery 21 to the image memory 18 and the communication unit 24.

Thereafter, when the state of operation of the radiographic image detection device 5 reaches the state of operation just-before charging the rechargeable battery 21, the control unit 27 sends to the console 6, not only the state of operation of the radiographic image detection device 5, but also various information such as charge quantity of the rechargeable battery 21 of the radiographic image detection device 5 (step SC12).

Subsequently, the control unit 27 judges whether the state of operation just-before charging radiographic image detection device 5 was the imaging ready state and the state of operation of the radiographic image detection device 5 is actually the imaging ready state (step SC13), and as a result of such judgment, the state of operation of the radiographic image detection device 5 is actually at the imaging ready state (step SC13; YES), for preparation of new imaging, performs initialization operation such as resetting the stored image information and dark-image reading operation (step SC14). If it is judged that state of operation is not at imaging ready state (step SC13; NO), the operation returns step SC1.

Subsequently, the control unit 27 repeatedly judges whether radiographic imaging has been initiated by the operator (step SC15), and as a result of such judgment, judged that radiographic imaging has been initiated (step SC15; YES), the operation will progress to step SC16. When actual radiographic imaging starts, the radiation source 12 emits the radiation, and the control unit 27 operates the scan drive circuit 16 to send the pulses to each photoelectric conversion elements, thus scanning and driving the respective photoelectric conversion elements, and also reads the electric energy stored in the respective photoelectric conversion elements with the signal reading circuit 17 to obtain radiographic image information of (step SC16).

After obtaining the radiographic image information, the control unit 27 stores the radiographic image information of the subject 9 in the image memory 18, and transmits the image information to the console 6 (step SC17). Each operation described in steps SC1 through SA17 is repeated.

Continuously, within console 6, control unit 29 judges whether it received information that charge quantity is of the rechargeable battery 21 is less than the predetermined amount (step SD1), through the operation of the above mentioned step SC3 by the control unit 27 of the radiographic image detection device 5. As a result of the judgment, when the control unit 29 receives information that charge quantity of the rechargeable battery 21 is less than the predetermined amount (step SD1; YES), it warns the operator by means such as displaying a message that the charge quantity is less than the predetermined amount on the display unit 32 (step SD2). Console 6 may also receive the charge quantity of the rechargeable battery 21 as a signal constantly from the radiographic image detection device 5, and the control unit 29 may display the charge quantity of the rechargeable battery 21 on the display unit 32 constantly depending on the signal received.

On the contrary, when the control unit 29 does not receive information that charge quantity of the rechargeable battery 21 is less than the predetermined amount (step SD1; NO), it judges whether it has received a message that charging of the rechargeable battery 21 has completed, depending on the operation of the mentioned step SA9 by the control unit 27 of the radiographic image detection device 5 (step SD3). As a result of the judgment, when the control unit 29 receives information that charging of the rechargeable battery 21 has completed (step SD3; YES), it displays a message that the charging of the rechargeable battery 21 has completed on the display unit 32 (step SD4).

On the other hand, when the control unit 29 judges that it has not received information that charging of the rechargeable battery 21 has completed (step SD3; NO), it judges whether it has received information concerning the state of operation of the radiographic image detection device 5, charge quantity of the rechargeable battery 21, and the like, depending on the operation of the mentioned step SC12 by the control unit 27 of the radiographic image detection device 5 (step SD5). As a result of the judgment, when the control unit 29 judges that it has received such information (step SD5; YES), it displays information concerning the state of operation of the radiographic image detection device 5, charge quantity of the rechargeable battery 21, and the like, on the display unit 32 (step SD6).

On the contrary, when the control unit 29 judges that it has not received information concerning the state of operation of the radiographic image detection device 5, charge quantity of the rechargeable battery 21, and the like (step SD5; NO), it judges whether it has received radiographic image signal, depending on the operation of the mentioned step SC17 by the control unit 27 of the radiographic image detection device 5 (step SD7). As a result of the judgment, when the control unit 29 judges that it has received such radiographic image signal (step SD7; YES), it performs predetermined image operation (step SD8) depending on the received signal, obtain thumb-nail image and a radiographic image that a doctor and the like desire, and displays radiographic image on the display unit 32 (step SD9).

The control unit 29 repeatedly performs the mentioned serial steps SD1-SD9 when operation described in step SD2, step SD4, step SD6, and step SD9 is concluded, including when it judges that it has not received radiographic image signal (step SD7; NO).

The entire disclosure of Japanese Patent Application No. 2004-269974 filed on Sep. 16, 2004 including specification, claims, drawings and abstract, of Japanese Patent Application No. 2005-23643 filed on Jan. 31, 2005 including specification, claims, drawings and abstract, and of Japanese Patent Application No. 2005-253659 filed on Jan. 31, 2005 including specification, claims, drawings and abstract, are incorporated herein by reference in its entirety.

What is claimed is:

1. A radiographic image detection device, which has a plurality of states of operation and detects irradiated radiation to obtain radiographic image information, the detection device comprising:
   a power supply source comprising a rechargeable or replaceable battery to supply power to a plurality of units driven by the power;
   a status memory to store information of operation concerning the state of operation after end of charging or replacing the battery; and
   a control unit that controls operation of the units driven by the power in response to the information of operation stored in the status memory after the end of charging or replacing the battery;
   wherein the plurality of states of operation include: an imaging ready state in which the detection device is capable of detecting the radiation; an imaging standby state which requires less power consumption than the imaging ready state and in which power is supplied to at least one of the units driven by the power; and an imaging stop state in which power supply is stopped for all of the units driven by the power; and
   wherein the imaging standby state has a plurality of imaging standby modes having different power consumption.

2. The radiographic image detection device of claim 1, wherein the state of operation after the end of charging or replacing the battery can be selectively set, and the control unit stores the information of operation in the status memory based on the selectively set state of operation.

3. The radiographic image detection device of claim 2, wherein it is selectable whether the state of operation after the end of charging or replacing the battery is previously set or arbitrarily set, and the control unit stores the information of operation in the status memory depending on the selected one of the previously set state of operation and the arbitrarily set state of operation.

4. The radiographic image detection device of claim 3, wherein the state of operation to be arbitrarily set is selectable from: the imaging ready state, the plurality of modes of the imaging standby state, and the imaging stop state.

5. The radiographic image detection device of claim 1, wherein the information of operation is stored in the status memory based on the state of operation just before the charging or replacement of the battery.

6. The radiographic image detection device of claim 1, wherein, while the battery is being charged or replaced, the control unit controls the operation of the units driven by the power so that the detection device is in one of the imaging standby modes that requires minimum power consumption among the plurality of imaging standby modes.

7. The radiographic image detection device of claim 1, wherein the battery is replaceable, and the power supply source is brought into a turned-off state while the battery is being detached or attached.

8. The radiographic image detection device of claim 1, wherein the detection device is a cassette flat panel detector which detects the irradiated radiation, converts the radiation into electric signals and stores the electric signals, reads the stored electric signals, and obtains radiographic image information.

9. A radiographic imaging system comprising:
a radiographic image detection device which has a plurality of states of operation and detects irradiated radiation to obtain radiographic image information, and which comprises a power supply source comprising a rechargeable or replaceable battery to supply power to a plurality of units driven by the power;
a console capable of communicating with the radiographic image detection device; and
a status memory to store information of operation concerning the state of operation of the radiographic image detection device after end of charging or replacing the battery;
wherein the information of operation is stored in the status memory before the end of charging or replacing the battery, and the radiographic image detection device further comprises a control unit to control operation of the units driven by the power in response to the information of operation stored in the status memory after the end of charging or replacing the battery;
wherein the plurality of states of operation include: an imaging ready state in which the radiographic image detection device is capable of detecting the radiation; an imaging standby state which requires less power consumption than the imaging ready state and in which power is supplied to at least one of the units driven by the power; and an imaging stop state in which power supply is stopped for all of the units driven by the power; and
wherein the imaging standby state has a plurality of imaging standby modes having different power consumption.

10. The radiographic imaging system of claim 9, wherein the state of operation after the end of charging or replacing the battery can be selectively set, and the information of operation is stored in the status memory based on the selectively set state of operation.

11. The radiographic image system of claim 10, wherein it is selectable whether the state of operation after the end of charging or replacing the battery is previously set or arbitrarily set, and the information of operation is stored in the status memory depending on the selected one of the previously set state of operation and the arbitrarily set state of operation.

12. The radiographic imaging system of claim 11, wherein the state of operation to be arbitrarily set is selectable from: the imaging ready state, the plurality of modes of the imaging standby state, and the imaging stop state.

13. The radiographic imaging system of claim 9, wherein the information of operation is stored in the status memory based on the state of operation just before the charging or replacement of the battery.

14. The radiographic imaging system of claim 9, wherein, while the battery is being charged or replaced, the control unit controls the operation of the units driven by the power so that the detection device is in one of the imaging standby modes that requires minimum power consumption among the plurality of imaging standby modes.

15. The radiographic imaging system of claim 9, wherein the battery is replaceable, and the detection device is brought into a turned-off state while the battery is being detached or attached.

16. The radiographic imaging system of claim 9, wherein the radiographic image detection device is a cassette flat panel detector which detects the irradiated radiation, converts the radiation into electric signals and stores the electric signals, reads the stored electric signals, and obtains radiographic image information.

* * * * *